Figure 3A:
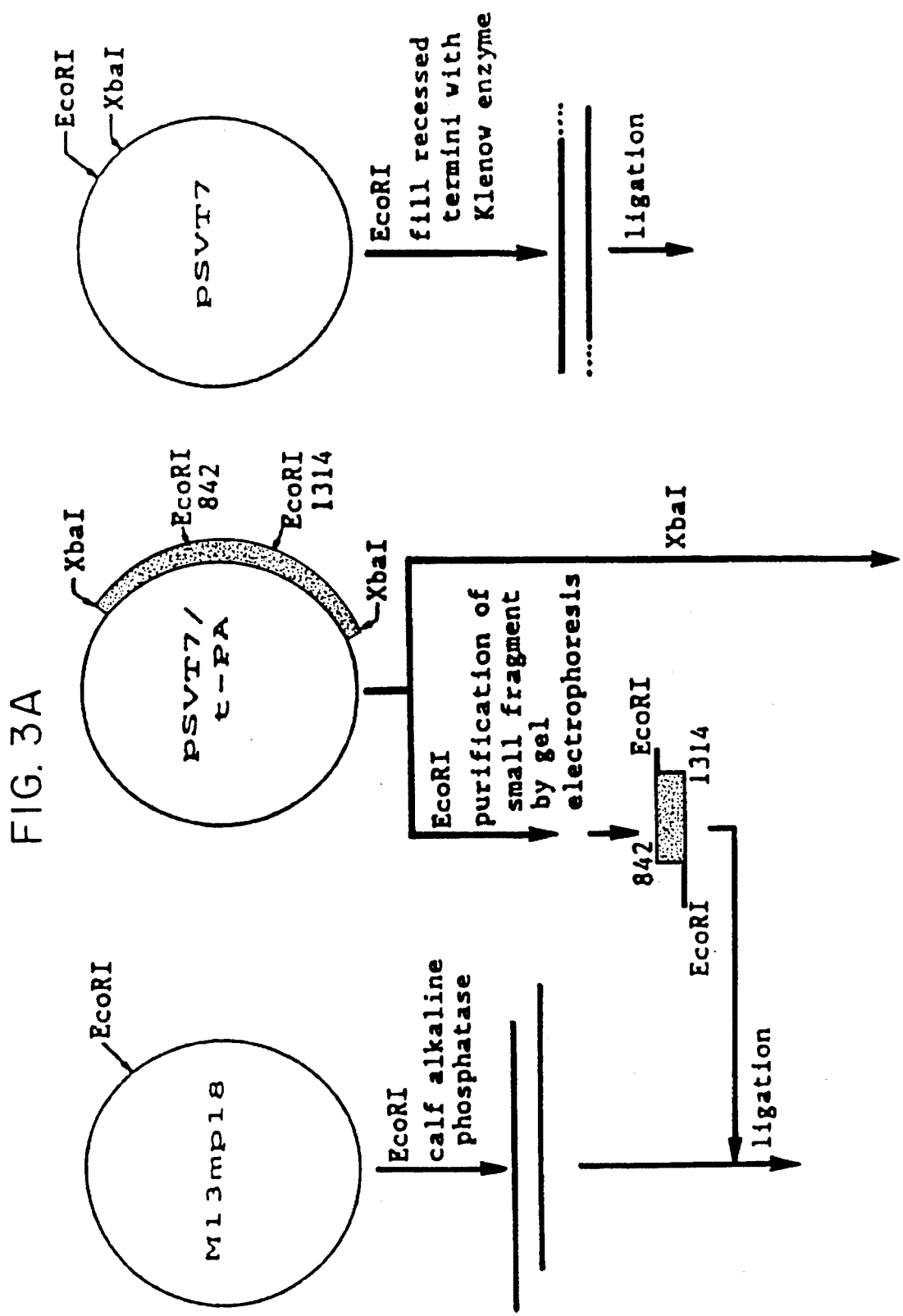

US005550042A

United States Patent [19]
Sambrook et al.

[11] Patent Number: 5,550,042
[45] Date of Patent: Aug. 27, 1996

[54] SERINE PROTEASE MUTANTS OF THE CHYMOTRYPSIN SUPERFAMILY RESISTANT TO INHIBITION BY THEIR COGNATE INHIBITORS AND GENES ENCODING THE SAME AND SERINE PROTEASE INHIBITOR MUTANTS AND GENES ENCODING THE SAME

[75] Inventors: Joseph F. Sambrook; Edwin L. Madison; Elizabeth J. Goldsmith; Maryjane H. Gething; Robert D. Gerard, all of Dallas, Tex.

[73] Assignee: The Board of Regents of The University of Texas System, Austin, Tex.

[21] Appl. No.: 434,748

[22] Filed: Nov. 13, 1989

Related U.S. Application Data

[63] Continuation-in-part of Ser. No. 319,212, Mar. 6, 1989, abandoned.

[51] Int. Cl.⁶ ............................ C12N 15/01; C12N 15/63; C12N 9/50; C07H 21/04
[52] U.S. Cl. ................................... 435/172.1; 435/320.1; 435/212; 435/69.1; 530/380; 536/23.2; 536/23.5
[58] Field of Search ...................................... 435/212, 213, 435/214, 215, 320, 320.1, 172.1, 69.7, 91.1; 530/380, 381, 382, 383, 300, 370; 536/27, 23.2, 23.5

[56] References Cited

U.S. PATENT DOCUMENTS

| | | | |
|---|---|---|---|
| 5,073,494 | 12/1991 | Heyneker et al. | 435/226 |
| 5,108,901 | 4/1992 | Anderson et al. | 435/23 |
| 5,200,340 | 4/1993 | Foster et al. | 424/94.64 |
| 5,262,170 | 11/1993 | Anderson | 424/94.64 |
| 5,405,771 | 4/1995 | Anderson | 435/240.2 |

FOREIGN PATENT DOCUMENTS

| | | | |
|---|---|---|---|
| 0093619 | 11/1983 | European Pat. Off. | C12N 15/00 |
| 0292009 | 11/1988 | European Pat. Off. | C12N 9/50 |
| 9002798 | 3/1990 | WIPO | C12N 9/64 |

OTHER PUBLICATIONS

Bergum et al, "Neutralization by Plasmiogen Activator Inhibitor-1 of Mutants of Tissue Plasminogen Activator", *Enzyme*, 40:122–129 (1988).
Haigwood et al, "Improvements of T-PA Properties by Means of Site directed Mutagenesis", *Throm Haemostas*, 58:1042 (1987).
Read, R. J. et al, *In: Proteinase Inhibitors*, Ed. Barret, A. J. et al, Elsevier, Amsterdam, pp. 301–336 (1986).
Blundell, T. et al, *Nature*, 326:347–352 (1987).
Huber, R. et al, *J. Mol. Biol.*, 89:73–101 (1974).
Bode, W. et al, *In: Proteolysis and Physiological Regulation*, Academic Press, New York, pp. 43–76 (1976).
Greer, *Proteins: Structure, Function, and Genetics*, 7:317–334 (1990).
Swindells et al, *Current Opinion in Biotechnology*, 2:512–519 (1991).
Argos et al, *Protein Engineering*, 4:375–383 (1991).
Rastetter, *Trends in Biotechnology*, 1:80–84 (1983).
Ackers et al, *Ann. Rev. Biochem.*, 54:597–629 (1985).
Rickles et al, *J. Biol. Chem.*, 263:1563–1569 (1988).
Gardell et al, *J. Biol. Chem.*, 264:17947–17952 (1989).
Belin et al, *Eur. J. Biochem.*, 148:225–232 (1985).
Bennett et al, *J. Biol. Chem.*, 266:1–11 (1991).

(List continued on next page.)

*Primary Examiner*—Mindy Fleisher
*Assistant Examiner*—Nancy J. Degen
*Attorney, Agent, or Firm*—Sughrue, Mion, Zinn, Macpeak & Seas

[57] ABSTRACT

The present invention relates to serine protease mutants of the chymotrypsin superfamily that are resistant to inhibition by their cognate inhibitors, and genes that encode the same. The present invention also relates to serine protease inhibitor mutants that inhibit the serine protease mutants of the present invention, and genes that encode the same. The serine protease, mutants and serine protease inhibitor mutants are useful as, e.g., pharmacological agents.

48 Claims, 15 Drawing Sheets

OTHER PUBLICATIONS

Adams et al, *J. Biol. Chem.*, 266:8476–8482 (1991).
Madison et al, *Nature*, 339:721–723 (Jun. 1989).
Madison et al *J. Biol. Chem.*, 265:21423–21426 (Dec. 1990).
Larsen et al, *Current Opinion in Biotechnology*, 2:220–226 (1991).
Ringe, *Nature*, 339:658–659 (1989).
Barrett et al, Eds., *Proteinase Inhibitors*, Elsevier Science Publishers (Amsterdam), pp. 403–420 (1986).
Kraut, *Ann. Rev. Biochem.*, 46:311–358 (1977).
Matheson et al, *J. Biol. Chem.*, 261:10404–10409 (1986).
Strassburger et al, *FEBS Lett.*, 157:219–223 (1983).
Holmes et al, *Biochem.*, 26:5133–5140 (1987).
Schapira et al, *J. Clin. Invest.*, 76:635–637 (1985).
Owen et al, *New Eng., J. Med.*, 309:694–698 (1983).
Braun et al, *Biochem.*, 27:6517–6524 (1988).
Schapira et al, *J. Clin. Invest.*, 80:582–585 (1987).

FIG. 1

```
                                  16                                    39             50
TRYPSIN              ..........  IVGGYTCGAN  TVPYQVSLNS  .......GYH  FCGGSLINSQ
                                                            296    302
TPA LT.CHAIN         ..........  IKGGLFADIA  SHPWQAAIFA  KHRRSPGERF  LCGGILISSC
UROKINASE            ..........  IGGEFTTIEN  Q.PWFAAIYR  RHRGGS.VTY  VCGGSLMSPC
PLASMIN              ..........  VVGGCVAHPH  SWPWQVSLRT  .....RFGMH  FCGGTLISPE
PROTEIN C            DQEDQVDPRL  IDGKMTRRGD  S.PWQVVLLD  .....SKKKL  ACGAVLIHPS
THROMBIN             ..........  IVEGQDAEVG  LSPWQVMLFR  ....KSPQEL  LCGASLISDR

57
TRYPSIN              WVVSAAHCYK  S.....GIQV  RLGEDNINVV  EG.NEQFISA  SKSIVH....
                         322                                    350
TPA LT. CHAIN        WILSAAHCFQ  ERFPPHHLTV  ILGR.TYRVV  PGEEEQKFEV  EKYIVHK...
UROKINASE            WVISATHCFI  DYPKKEDYIV  YLGR.SRLNS  NTQGEMKFEV  ENLILHK...
PLASMIN              WVLTAAHCLE  KSPRPSSYKV  ILGA.HQEVN  LEPHVQEIEV  SRLFL.....
PROTEIN C            WVLTAAHCMD  ESKKLL...V  RLGEYDLRRW  EKWEL.DLDI  KEVFVH....
THROMBIN             WVLTAAHCLL  YPPWDK...N  FTVDDLLVRI  GKHSRTRYER  KVEKISMLDK

102
TRYPSIN              .....PSYNS  NTLNNDIMLI  KLKSA.....  ASLNSRVASI  SLPTSCASAG
                                   371                                   400
TPA LT. CHAIN        ......EFDD  DTYDNDIALL  QLKSDSSRCA  QESSV.VRTV  CLPPADLQLP
UROKINASE            ....DYSADT  LAHHNDIALL  KIRSKEGRCA  QPSRT.IQTI  CLPSMYNDPQ
PLASMIN              ..........  EPTRKDIALL  KLSSP.....  AVITDKVIPA  CLPSPNYVVA
PROTEIN C            .....PNYSK  STTDNDIALL  HLAQP.....  ATLSQTIVPI  CLPDSGLAER
THROMBIN             IYIHPRYNWK  ENLDRDIALL  KLKRP.....  IELSDYIHPV  CLPDKQTAAK

150
TRYPSIN              ......TQCL  ISGWGNTKSS  GT.SYPDVLK  CLKAPILSDS  SCKSAYPGQ.
TPA LT. CHAIN        DW....TECE  LSGYGKHEAL  SP.FYSERLK  EAHVRLYPSS  RCTSQHLLNR
UROKINASE            FG....TSCE  ITGFGKENST  DY.LYPEQLK  MTVVKLISHR  ECQQPHYYGS
PLASMIN              DR....TECF  ITGWGETQGT  ...FGAGLLK  EAQLPVIENK  VCNRYEFLNG
PROTEIN C            ELNQAGQETL  VTGWGYHSSR  E.KEAKRNRT  FVLNFIKIPV  VPHNECSEVM
THROMBIN             LLH.AGFKGR  VTGWGNRRET  WTTSVAEVQP  SVLQVVNLPL  VERPVCKAST 195    200
TRYPSIN              ...ITSNMFC  AGYL.EGG..  ...KDSCQGD  SGGPVVCS..  ....GKLQGI
                         450                                478
TPA LT. CHAIN        T..VTDNMLC  AGDTRSGGPQ  ANLHDACQGD  SGGPLVCLND  ..GRMTLVGI
UROKINASE            E..VTTKMLC  AAD.....PQ  .WKTDSCQGD  SGGPLVCSLQ  ..GRMTLTGI
PLASMIN              R..VQSTELC  AGHL......  ..ATDSCQGD  SGGPLVCFEK  ..DKYILQGV
PROTEIN C            SNMVSENMLC  AGIL......  GDRQDACEGD  SGGPMVASFH  ..GTWFLVGL
THROMBIN             RIRITDNMFC  AGYK...PGE  GKRGDACEGD  SGGPFVMKSP  YNNRWYQMGI 214                                    245
TRYPSIN              VSWGSGCAQK  NKPGVYTKVC  NYVSWIKQTI  ASN........  ..
                         500                                527
TPA LT. CHAIN        ISWGLGCGQK  DVPGVYTKVT  NYLDWIRDNM  RP.........  ..
UROKINASE            VSWGRGCALK  DKPGVYTRVS  HFLPWIRSHT  KEENGLAL...  ..
PLASMIN              TSWGLGCARP  NKPGVYVRVS  RFVTWIEGVM  RNN........  ..
PROTEIN C            VSWGEGCGLL  HNYGVYTKVS  RYLDWIHGHI  RDKEAPQKSW  AP
THROMBIN             VSWGEGCDRD  GKYGFYTHVF  RLKKWIQKVI  DRLGS......  ..
```

FIG. 2A

```
PAI-1         ..........  ..........  ..........  ..........  ..........  ..........
Antitrypsin   ..........  ..........  ..........  ..........  ..........  ..........
PAI-2         ..........  ..........  ..........  ..........  ..........  ..........
A-chymotryp   ..........  ..........  ..........  ..........  ..........  ..........
A2-antiplas   ..........  ..........  ..........  ..........  ..........  ..........
A-thrombIII   ..........  ..........  ...GSKGPLD  QLEKGGETAQ  SADPQWEQLN  NKNLSMPLLP
HeparinCoII   NPNATSSSSQ  DPESLQDRGE  GKVATTVISK  MLFVEPILEV  SSLPTTNSTT
Clinhibitor   ..........  ..........  ..........  ..........  ..........  ..........

1
PAI-1         ..........  ..........  ..........  ..........  ..........  .VHHPPSY
Antitrypsin   ..........  ..........  ..........  ..........  ..........  .....EDPQGD
                                                                              1
PAI-2         ..........  ..........  ..........  ..........  ..........  ...NSPLD
A-chymotryp   ..........  ..........  ..........  .....NQE    QVSPLTLLKL  GNQEPGGQTA
A2-antiplas   ..........  ....CHGSPV  DICTAKPRDI  PMNPMCIYKS  PEKKATEDEG
A-thrombIII   ....NDWIPEGEED  DDYLDLEKIF  SEDDDYIDIV  DSLSVSPTDS
HeparinCoII   ADFHKENTVT  TDEPTTQPTT  EPTTQPTIQP  TQPTTQLPTD  SPTQPTTGSF
Clinhibitor   NSATKITANT
```

FIG. 2B

```
PAI-1         VAHLA.....  ..........  ...SDFGVR   VFQQVAQ.AS  KDRNVVFSPY
Antitrypsin   AAQKTDTSHH  DQDHPTFNKI  TPNLAEFAFS  LYRQLAH.QS  NSTNIFFSPV
                                                              50
PAI-2         ..........  ...MEDLCVA  NTLFALNLFK  HLAK.ASPTQ  NLFLSPWSIS
A-chymotryp   EENLTQENQD  RGTHVDLGLA  SANV.DFAFS  LYKQLVL.KA  LDKNVIFSPL
A2-antiplas   LKSPPGVCSR  DPTPEQTHRL  ARAMMAFTAD  LFSLVAQ.TS  TCPNLILSPL
A-thrombIII   ...SEQKIP   EATNRRVWEL  SKANSRFATT  FYQHLADSKN  DNDNIFLSPL
HeparinCoII   DVSAGNILQL  FHGKSRIQRL  NILNAKFAFN  LYRVLKDQVN  TFDNIFIAPV
Clinhibitor   CPGPVTLCSD  LESHSTEAVL  GDALVDFSLK  LYHAFSAMKK  VETNMAFSPF
                                      50

PAI-1         GVASVLAMLQ  LTTGGETQQQ  IQAAMGFKID  D.........  ..........
Antitrypsin   SIATAFAMLS  LGTKADTHDE  ILEGLNFNLT  E.........  ..........

PAI-2         STMAMVYMGS  RGSTEDQMAK  VLQFNEVGAN  AVTPMTPENF  TSCGFMQQIQ
A-chymotryp   SISTALAFLS  LGAHNTTLTE  ILKASSSPHG  D.........  ..........
A2-antiplas   SVALALSHLA  LGAQNHTLQR  LQQVLHAGSG  P.........  ..........
A-thrombIII   SISTAFAMTK  LGACNDTLQQ  LMEVFKFDTI  SEKTSDQIHF  ..........
HeparinCoII   GISTAMGMIS  LGLKGETHEQ  VHSILHFKDF  VN........  ..........
Clinhibitor   SIASLLTQVL  LGAGQNTKTN  LESILSYPKD  FTCVHQALKG  F.........
```

FIG. 2C

|                | | | | | | 100 |
|---|---|---|---|---|---|---|
| PAI-1          | ............ | ............ | ......KGM | APALRHLYKE | LMGPWNKDE. | ISTTDAIFVQ |
| Antitrypsin    | ............ | ............ | ....IPEAQI | HEGFQELLRT | LNQPDSQLQ. | LTTDGGLFLS |
|                | | | | 100 | | |
| PAI-2          | KGSYPDAILQ | AQAADKIHSS | FRSLSSAINA | STGDYL.LES | VNKLFGEKSA |
| A-chymotryp    | ............ | ....LLRQKF | TQSFQHLRAP | SISSSDELQ. | LSMGNAMFVK |
| A2-antiplas    | ............ | ............ | ..CLPHLLSR | LCQDLGPGA. | FRLAARMYLQ |
| A-thrombIII    | ............ | ............ | ..FFAKLNCR | LYRKANKSSK | LVSANRLFGD |
| HeparinCoII    | ............ | ASSKYEITTI | HNLFRKLTHR | LFRRNFGYT. | LRSVNDLYIQ |
| Clinhibitor    | ............ | ............ | ............ | ......TTKG | VTSVSQIFHS |
| PAI-1          | RDLKLVQGFM | PHFFRLFRST | VKQVDFSE.V | ERARFIINDW | VKTHTKGMIS |
| Antitrypsin    | EGLKLVDKFL | EDVKKLYHSE | AFTVNFGD.T | EEAKKQINDY | VEKGTQGKIV |
|                | | | 150 | | |
| PAI-2          | SFREEYIRLC | QKYYSSEPQA | VDFLECAEEA | RKKINSWVKT | QTKGKIPNLL |
| A-chymotryp    | EQLSLLDRFT | EDAKRLYGSE | AFATDFQD.S | AAAKKLINDY | VKNGTRGKIT |
| A2-antiplas    | KGFPIKEDFL | EQSEQLFGAK | ..PVSLTGKQ | EDDLANINQW | VKEATEGKIQ |
| A-thrombIII    | KSLTFNETYQ | DISELVYGAK | LQPLDFKENA | EQSRAAINKW | VSNKTEGRIT |
| HeparinCoII    | KQFPILLDFK | TKVREYYFAE | AQIADFSD.. | PAFISKTNNH | IMKLTKGLIK |
| Clinhibitor    | PDLAIRDTFV | NASRTLYSSS | PRVLSNNS.. | DANLELINTW | VAKNTNNKIS |

FIG. 2D

```
                    150
PAI-1        NLLGKGAVDQ LTRLVLVNAL YFNGQWKTPF PDSSTHRRLF HKSDGSTVSV
Antitrypsin  DLV..KELDR DTVFALVNYI FFKGKWERPF EVKDTEEEDF HVDQVTTVKV
                                                 200
PAI-2        PEGSVDGDTR MVLVNAVYFK GKWKTPFEKK LNGLYPFRVN SAQRTPVQMM
A-chymotryp  DLI..KDPDS QTMMVLVNYI FFKAKWEMPF DPQDTHQSRF YLSKKKWVMV
A2-antiplas  EFLS..GLPE DTVLLLLNAI HFQGFWRNKF DPSLTQRDSF HLDEQFTVPV
A-thrombIII  DVIPSEAINE LTVLVLVNTI YFKGLWKSKF SPENTRKELF YKADGESCSA
HeparinCoII  DALE..NIDP ATQMMILNCI YFKGSWVNKF PVEMTHNHNF RLNEREVVKV
ClInhibitor  RLLD..SLPS DTRLVLLNAI YLSAKWKTTF DPKKTRMEPF HFKNSVIKVP 200
PAI-1        PMMAQTNKFN YTEFTTPDGH YDILELPYH. GDTLSMFIAA PYEKE..VPL
Antitrypsin  PMMKRLGMFN IQHC..KKLSS W..VLLMKYL GNANAIFFLP DEGK......L
                                                 250
PAI-2        YLREKLNIGY IEDLKAQ... ILELPYAGDV SMFLLLPDEI ADVSTGLELL
A-chymotryp  PMMSLHHLTI PYFRDEELSC ..TVVELKYT GNASALFILP DQDK......M
A2-antiplas  EMMQARTYPL RWFLLEQPEI ..QVAHFPFK NNMSFVVLVP TH......FEW
A-thrombIII  SMMYQEGKFR YRR..VAEGT ..QVLELPFK GDDITMVLIL PK......PEK
HeparinCoII  SMMQTKGNFL AANDQELDCD ...ILQLEYV GGISMLIVVP HKM.....SGM
ClInhibitor  MMNSKKYPVA HFIDQTLKAK .VGQLQL..S HNLSLVILVP QNLK....HRL
```

FIG. 2E

```
                   250
PAI-1         SALTNILSAQ LISHWKGNMT ..RLPRLLVL PKFSLETEVD LR.KPLENLG
Antitrypsin   QHLENELTHD IITKFLENED ..RRSASLHL PKLSITGTYD LK.SVLGQLG
                                                        300
PAI-2         ESEITYDKLN KWTSKDKMAE DEVEVYIPQF KLEEHYELR. SILRSMGMED
A-chymotryp   EEVEAMLLPE TLKRWRDSLE F.REIGELYL PKFSISRDYN LN.DILLQLG
A2-antiplas   NVSQVLANLS WDTLHPPLVW ..ERPTKVRL PKLYLKHQMD LV.ATLSQLG
A-thrombIII   SLAKVEKELT PEVLQEWLDE LEEMMLVVHM PRFRIEDGFS LK.EQLQDMG
HeparinCoII   KTLEAQLTPR VVERWQKSMT ..NRTREVLL PKFKLEKNYN LV.ESLKLMG
Clinhibitor   EDMEQALSPS VFKAIMEKLE MSKFQPTLLT LPRIKVTTSQ DMLSIMEKLE 300
PAI-1         MTDMFRQ... FQADFTSLSD QEPLHVAQAL QKVKIEVNES GTVASSST..
Antitrypsin   ITKVFSN... .GADLSGVTE EAPLKLSKAV HKAVLTIDEK GTEAAGAM..
                                                        350
PAI-2         AFNK...GRA NFSGMSERND LFLSEVFHQA MVDVNEEGTE AAAGTGGV..
A-chymotryp   IEEAFTS... .KADLSGITG ARNLAVSQVV HKVVSDVFEE GTEASAAT..
A2-antiplas   LQELFQA... ..PDLRGISE Q.SLVVSGVQ HQSTLELSEV GVEAAAAT..
A-thrombIII   LVDLFSPEKS KLPGIVAEGR D.DLYVSDAF HKAFLEVNEE GSEAAAST..
HeparinCoII   IRMLFD.... .KNGNMAGIS DQRIAIDLFK HQGTITVNEE GTQATTVT..
Clinhibitor   FFDFSYD... ..LNLCGLTE DPDLQVSAMQ HQTVLELTET GVEAAAAS..
```

FIG. 2F

```
                                          350
PAI-1          AVIVSARMAP EE.....IIMD RPFLFVVRHN PTGTVLFMGQ VMEP......
Antitrypsin    FLEAIPMSIP PE.....VKFN KPFVFLMIEQ NTKSPLFMGK VVNPTQK...

PAI-2          ...MTGRTGH GGPQ..FVAD HPFLFLIMHK ITKCILFFGR FCSP......
A-chymotryp    AVKITLLSAL VETRTIVRFN RPFLMIIVPT DTQNIFFMSK VTNP.SKPRA
A2-antiplas    .SIAMSRMSL SS....FSVN RPFLFFIFED TTGLPLFVGS VRNPNPSAPR
A-thrombIII    AVVIAGRSLN PNRVT.FKAN RPFLVFIREV PLNTIIFMGR VANPCVK...
HeparinCoII    TVGFMPLSTQ VR.....FTVD RPFLFLIYEH RTSCLLFMGR VANPSRS...
ClInhibitor    .AISVARTLL V......FEVQ QPFLFVLWDQ QHKFPVFMGR VYDPRA....

PAI-1          .......... .......... .......... .......... ..........
Antitrypsin    .......... .......... .......... .......... ..........

PAI-2          CIKQWGSQ.. .......... .......... .......... ..........
A-chymotryp    ELKEQQDSPG NKDFLQSLKG FPRGDKLFGP DLKLVPPMEE DYPQFGSPK
A2-antiplas    .......... .......... .......... .......... ..........
A-thrombIII    .......... .......... .......... .......... ..........
HeparinCoII    .......... .......... .......... .......... ..........
ClInhibitor    .......... .......... .......... .......... ..........
```

5,550,042

SERINE PROTEASE MUTANTS OF THE CHYMOTRYPSIN SUPERFAMILY RESISTANT TO INHIBITION BY THEIR COGNATE INHIBITORS AND GENES ENCODING THE SAME AND SERINE PROTEASE INHIBITOR MUTANTS AND GENES ENCODING THE SAME

CROSS-REFERENCE TO RELATED APPLICATIONS

This is a continuation-in-part of U.S. patent application Ser. No. 07/319,212, filed Mar. 6, 1989, now abandoned.

FIELD OF THE INVENTION

The present invention relates to serine protease mutants of the chymotrypsin superfamily that are resistant to inhibition by their cognate inhibitors, and genes that encode the same. The present invention also relates to serine protease inhibitor mutants that inhibit the serine protease mutants of the present invention, and genes that encode the same. The serine protease mutants and serine protease inhibitor mutants are useful as, e.g., pharmacological agents.

BACKGROUND OF THE INVENTION

I. Serine Proteases

Serine proteases (E.C. 3.4.21) are the sub-sub class of endopeptidases that use serine as the nucleophile in peptide bond cleavage (Barrett, A. J., *In: Proteinase Inhibitors*, Ed. Barrett, A. J. et al, Elsevier, Amsterdam, pages 3–22 (1986); and Hartlay, B. S., *Ann. Rev. Blochem.*, 29:45–72 (1960)).

Serine proteases are well known in the art and two superfamilies of serine proteases, i.e., the chymotrypsin superfamily and the Streptomyces subtilisin superfamily, have been observed to date (Barrett, A. J., *In: Proteinase Inhibitors*, Ed. Barrett, A. J. et al, Elsevier, Amsterdam, pages 3–22 (1986); and James, M. N. G., *In: Proteolysis and Physiological Regulation*, Ed. Ribbons, D. W. et al, Academic Press, New York, pages 125–142 (1976)).

Examples of serine proteases of the chymotrypsin superfamily include tissue-type plasminogen activator (hereinafter "t-PA"), trypsin, trypsin-like protease, chymotrypsin, plasmin, elastase, urokinase (or urinary-type plasminogen activator (hereinafter "u-PA")), acrosin, activated protein C, Cl esterase, cathepsin G, chymase and proteases of the blood coagulation cascade including kallikrein, thrombin, and Factors VIIa, IXa, Xa, XIa and XIIa (Barrett, A. J., *In: Proteinase Inhibitors*, Ed. Barrett, A. J. et al, Elsevier, Amsterdam, pages 3–22 (1986); Strassburger, W. et al, *FEBS Lett.*, 157:219–223 (1983); Dayhoff, M. O., *Atlas of Protein Sequence and Structure*, Vol. 5, National Biomedical Research Foundation, Silver Spring, Md. (1972); and Rosenberg, R. D. et al, *Hosp. Prac.*, 21:131–137 (1986)).

Some of the serine proteases of the chymotrypsin superfamily, including t-PA, plasmin, u-PA and the proteases of the blood coagulation cascade, are large molecules that contain, in addition to the serine protease catalytic domain, other structural domains responsible in part for regulation of their activity (Barrett, A. J., *In: Proteinase Inhibitors*, Ed. Barrett, A. J. et al, Elsevier, Amsterdam, pages 3–22 (1986); Gerard, R. D. et al, *Mol. Biol. Med.*, 3:449–457 (1986); and Blasi, F. et al, *In: Human Genes and Diseases*, Ed. Blasi, John Wiley & Sons, Ltd., pages 377–414 (1986)).

The catalytic domains of all of the serine proteases of the chymotrypsin superfamily have both sequence homology and structural homology. The sequence homology includes the total conservation of:
(i) the characteristic active site residues (e.g., $Ser_{195}$, $His_{57}$ and $Asp_{102}$ in the case of trypsin);
(ii) the oxyanion hole (e.g., $Gly_{193}$, $Asp_{194}$ in the case of trypsin); and
(iii) the cysteine residues that form disulfide bridges in the structure (Hartley, B. S., *Symp. Soc. Gen. Microbiol.*, 24:152–182 (1974)).

The structural homology includes:
(i) the common fold that consists of two Greek key structures (Richardson, J., *Adv. Prot. Chem.*, 34:167–339 (1981));
(ii) a common disposition of catalytic residuest and
(iii) detailed preservation of the structure within the core of the molecule (Stroud, R. M., *Sci. Am.*, 231:24–88 (1974)).

A comparison of the sequences of the members of the chymotrypsin superfamily reveals the presence of insertions or deletions of amino acids within the catalytic domains (see for example, FIG. 1). In all cases, these insertions or deletions map to the surface of the folded molecule and thus do not effect the basic structure of the molecule (Strassburger, W. et al, *FEBS Lett.*, 157:219–223 (1983)).

II. Serine Protease Inhibitors

Serine protease inhibitors are well known in the art and are divided into the following families: (i) the bovine pancreatic trypsin inhibitor (Kunitz) family, also known as basic protease inhibitor (Ketcham, L. K. et al, *In: Atlas of Protein Sequence and Structure*, Ed. Dayhoff, M. O., pages 131–143 (1978) (hereinafter "BPTI"), (ii) the Kazal family, (iii) the Streptomyces subtilisin inhibitor family (hereinafter "SSI"), (iv) the serpin family, (v) the soybean trypsin inhibitor (Kunitz) family, (vi) the potato inhibitor family, and (vii) the Bowman-Birk family (Laskowski, M. et al, *Ann. Rev. Biochem.*, 49:593–626 (1980); Read, R. J. et al, *In: Proteinase Inhibitors*, Ed. Barrett, A. J. et al, Elsevier, Amsterdam, pages 301–336 (1986); and Laskowski, M. et al, *Cold Spring Harbor Symp. Quant. Biol.*, LII:545–553 (1987)).

Crystallographic data are available for a number of intact inhibitors including members of the BPTI, Kazal, SSI, soybean trypsin and potato inhibitor families, and for a cleaved form of the serpin alpha-1-antitrypsin (Read, R. J. et al, *In: Proteinase Inhibitors*, Ed. Barrett, A. J. et al, Elsevier, Amsterdam, pages 301–336 (1986)). Despite the fact that these serine protease inhibitors are proteins of diverse size and sequence, the intact inhibitors studied to date all have in common a characteristic loop extending from the surface of the molecule that contains the recognition sequence for the active site of the cognate serine protease (Levin, E. G. et al, *Proc. Natl. Acad. Sci. USA*, 80:6804–6808 (1983)). The structural similarity of the loops in the different serine protease inhibitors is remarkable (Papamokos, E. et al, *J. Mol. Biol.*, 158:515–537 (1982)). Outside of the active site loop, the serine protease inhibitors of different families are generally unrelated structurally, although the Kazal family and Streptomyces subtilisin family of inhibitors display some structural and sequence similarity.

Many of the serine protease inhibitors have a broad specificity and are able to inhibit both the chymotrypsin superfamily of proteases, including the blood coagulation serine proteases, and the Streptomyces subtilisin superfamily of serine proteases (Laskowski, M. et al, *Ann. Rev.*

*Biochem.*, 49:593–626 (1980)). The specificity of each inhibitor is thought to be determined primarily by the identity of the amino acid that is immediately amino-terminal to the site of potential cleavage of the inhibitor by the serine protease. This amino acid, known as the $P_1$ site residue, is thought to form an acyl bond with the serine in the active site of the serine protease (Laskowski, M. et al, *Ann. Rev. Biochem.*, 49:593–626 (1980)).

A. The BPTI Family

Serine protease inhibitors belonging to the BPTI family include BPTI, snake venom inhibitor, inter-alpha inhibitor, and the A4 amyloid precursor A4695 (Laskowski, M. et al, *Ann. Rev. Biochem.*, 49:593–626 (1980); Read, R. J. et al, *In: Proteinase Inhibitors*, Ed. Barrett, A. J. et al, Elsevier, Amsterdam, pages 301–336 (1986); and Ponte, P. et al, *Nature*, 331:525–527 (1988)). Examples of serine proteases and their cognate BPTI family inhibitors are listed in Table I below.

TABLE I

| Serine Protease | Cognate BPTI Inhibitor |
| --- | --- |
| Trypsin | BPTI |
|  | Snake venom inhibitor |
|  | Inter-alpha inhibitor |
| (Unknown) | A4 amyloid precursor A4695 |
|  | protease nexin II |

B. The Kazal Family

Serine protease inhibitors belonging to the Kazal family include pancreatic secretory inhibitor, ovomucoid and seminal plasma acrosin inhibitor (Laskowski, M. et al, *Ann. Rev. Biochem.*, 49:593–626 (1980); Read, R. J. et al, *In: Proteinase Inhibitors*, Ed. Barrett, A. J. et al, Elsevier, Amsterdam, pages 301–336 (1986); and Laskowski, M. et al, *Cold Spring Harbor Sym. Quant. Biol.*, LII:545–553 (1987)). Examples of serine proteases and their cognate Kazal family inhibitors are listed in Table II below.

TABLE II

| Serine Protease | Cognate Kazal Inhibitor |
| --- | --- |
| Trypsin | Pancreatic secretory inhibitor |
|  | Ovomucoid |
|  | Seminal plasma acrosin inhibitor |
| Acrosin | Ovomucoid |
|  | Seminal plasma acrosin inhibitor |

C. The Streptomyces Subtilisin Inhibitor

Serine protease inhibitors belonging to the Streptomyces subtilisin inhibitor family include inhibitors obtained from *Streptomyces albogriseolus* and plasminostreptin (Laskowski, M. et al, *Ann. Rev. Biochem.*, 49:593–626 (1980)). Examples of serine proteases and their cognate Streptomyces subtilisin class inhibitors are listed in Table III below.

TABLE III

| Serine Protease | Cognate SSI Inhibitor |
| --- | --- |
| Subtilisin BPN' | *Streptomyces albogriseolus* inhibitor |
| Plasmin | Plasminostreptin |
| Trypsin | Plasminostreptin |

D. The Serpin Family

Serine protease inhibitors belonging to the serpin family include the plasminogen activator inhibitors PAI-1, PAI-2 and PAI-3, C1 esterase inhibitor, alpha-2-antiplasmin, contrapsin, alpha-1-antitrypsin, antithrombin III, protease nexin I, alpha-1-antichymotrypsin, protein C inhibitor, heparin cofactor II and growth hormone regulated protein (Carrell, R. W. et al, *Cold Spring Harbor Symp. Quant. Bioi.*, 52:527–535 (1987); Sommer, J. et al, *Biochem.*, 26:6407–6410 (1987); Suzuki, K. et al, *J. Biol. Chem.*, 262:611–616 (1987); and Stump, D. C. et al, *J. Biol. Chem.*, 261:12759–12766 (1986)).

The inhibition of serine proteases by serpins has been reviewed in Travis, J. et al, *Ann. Rev. Biochem.*, 52:655–709 (1983); Carrell, R. W. et al, *Trends Biochem. Sci.*, 10:20–24 (1985); Sprengers, E. D. et al, *Blood*, 69:381–387 (1987); and *Proteinase Inhibitors*, Ed. Barrett, A. J. et al, Elsevier, Amsterdam (1986).

Examples of serine proteases and their cognate serpin inhibitors are listed in Table IV below.

TABLE IV

| Serine protease | Cognate Serpin Inhibitor |
| --- | --- |
| Activated protein C | Protein C inhibitor |
|  | PAI-1 |
| C1 esterase | C1 esterase inhibitor |
| Cathepsin G | Alpha-1-antitrypsin |
|  | Alpha-1-antichymotrypsin |
| Chymase | Alpha-1-antichymotrypsin |
| Chymotrypsin | Alpha-1-antichymotrypsin |
|  | Alpha-2-antiplasmin |
|  | Contrapsin |
| Coagulation factors | Antithrombin III |
| (VIIa, IXa, Xa, XIa, XIIa) | C1 esterase inhibitor |
| Elastase | Alpha-1-antitrypsin |
| Kallikrein | C1 esterase inhibitor |
|  | Alpha-1-antitrypsin |
| Plasmin | Alpha-2-antiplasmin |
| Thrombin | Antithrombin III |
|  | Heparin cofactor II |
| t-PA | PAI-1, PAI-2, PAI-3 |
| Trypsin | Alpha-1-antitrypsin |
|  | Growth hormone regulated protein |
| Trypsin-like protease | Protease nexin I |
| u-PA | PAI-1, PAI-2, PAI-3 |

E. The Soybean Trypsin Inhibitor Family

A single example of the soybean trypsin inhibitor family, purified from soybeans, has been sequenced. Its complex with bovine pancreatic trypsin has been studied (Sweet, R. M. et al, *Biochem.*, 13:4214–4228(1974)).

F. The Potato Inhibitor Family

Serine protease inhibitors belonging to the potato inhibitor family include inhibitors from potatoes, barley and leeches (Read, R. J. et al, *In: Proteinase Inhibitors*, Ed. Barrett, A. J. et al, Elsevier, Amsterdam, pages 301–336 (1986)). Examples of serine proteases and their potato inhibitors are listed in Table V below.

TABLE V

| Serine Protease | Potato Inhibitor |
| --- | --- |
| Chymotrypsin | Barley chymotrypsin inhibitor |
| Subtilisin Novo | Barley chymotrypsin inhibitor |
| Subtilisin Carlsberg | Leech inhibitor eglin |

G. The Bowman-Birk Inhibitor Family

Serine protease inhibitors belonging to the Bowman-Birk inhibitor family include homologous proteins from legumes (Laskowski, M. et al, *Ann. Rev. Biochem.*, 49:593–626 (1980)). Examples of serine proteases and their Bowman-Birk inhibitors are listed in Table VI below.

TABLE VI

| Serine Protease | Bowman-Birk Inhibitor |
|---|---|
| Trypsin | Lima bean inhibitor IV |
| Elastase | Garden bean inhibitor |
| Chymotrypsin | Adzuki bean inhibitor II |

III. Serine Protease-Inhibitor Complexes

Serine protease inhibitors of all families form stable 1:1 complexes with their cognate serine proteases. These complexes dissociate only slowly (hours to days) (Laskowski, M. et al, *Ann. Rev. Biochem.*, 49:593–626 (1980); and Levin, E. G., *Proc. Natl. Acad. Sci. USA*, 80:6804–6808 (1983)). For all serine protease inhibitors, except the serpins, the dissociation products are a mixture of the intact and cleaved inhibitor molecules. On the other hand, since dissociation of serine protease-serpin complexes appears to yield only cleaved inhibitor molecules, serpins are thought to utilize a mechanism somewhat distinct from that of the other serine protease inhibitors.

Structural data are available for several serine protease-inhibitor complexes, including trypsin-BPTI, chymotrysin-ovomucoid inhibitor, chymotrypsin-potato inhibitor, and Streptomyces subtilisin-Streptomyces subtilisin inhibitor (Read, R. J. et al, *In: Proteinase Inhibitors*, Ed. Barrett, A. J. et al, Elsevier, Amsterdam, pages 301–336 (1986)). Examination of these structures reveals remarkable similarities in the specific interactions between each inhibitor and its cognate serine protease, despite the diverse sequences of the inhibitors. This structural similarity has suggested in the present invention that even when crystal structures are not available, it may be possible to predict the amino acid interactions occurring between an inhibitor and its cognate serine protease.

As discussed above, the inhibitors contain a reactive center that serves as a competitive substrate for the active site of the serine protease. Attack on the peptide bond between the $P_1$-$P_1$ residues of the reactive center (e.g., $Arg_{346}$-$Met_{347}$ in the case of PAI-1) does not lead to the normal, rapid dissociation of the products from the serine protease but, rather, to the establishment of a stable serine protease-inhibitor complex, probably by formation of a covalent bond between the serine of the active site of the protease and the $P_1$ residue of the inhibitor (Laskowski, M. et al, *Ann. Rev. Biochem.*, 49:593–626 (1980)). This mechanism findicates that the reactive center of an inhibitor, such as PAI-1, must fit tightly and precisely into the active site of the serine protease. However, to date, there are no X-ray crystallographic data on PAI-1, its cognate serine protease, t-PA, or the t-PA/PAI-1 complex. Thus, the exact nature of the interactions between this pair of proteins is unknown. There is a similar lack of structural information about other serpins or serpin-serine protease complexes.

IV. Utility of Serine Proteases

A particularly important serine protease of the chymotrypsin superfamily is t-PA. t-PA is currently being used, via intracoronary or intravenous administration, to treat myocardial infarction, pulmonary embolism, and deep venous thrombosis, although it does not work directly to dissolve thrombi (blood clots). Rather, t-PA promotes clevage of the peptide bond between $Arg_{560}$ and $Val_{561}$ of plasminogen (Robbins, K. C. et al, *J. Biol. Chem.*, 242:2333–2342 (1967)), thereby converting the inactive zymogen into the powerful but non-specific protease, plasmin, which then degrades the fibrin mesh work of the blood clot (Bachmann, F. et al, *Semin. Throm. Haemost.*, 43:77–89 (1984); Gerard, R. D. et al, *Mol. Biol. Med.*, 3:449–557 (1986); and Verstracte, M. et al, *Blood*, 67:1529–1541 (1986)).

t-PA produces local fibrinolysis without necessarily depleting systemic fibrinogen. This is because t-PA has the ability to bind directly to fibrins forming a fibrin-t-PA complex whose affinity for plasminogen is increased approximately 500 fold (Ranby, M. et al, *Biochim.Biophys. Acta*, 704:461–469 (1982); and Rijken, D. C. et al, *J. Biol. Chem.*, 257:2920–2925 (1982)). Thus, binding of intravenously-administered t-PA to coronary thrombi, where plasminogen is also present in high concentration (Wiman, B. et al, *Nature*, 272:549–550 (1978)), results in efficient production of plasmin at the site of the thrombus where it will do the most good.

At present, t-PA is administered in the form of an initial bolus that is followed by sustained infusion. The total amount of enzyme administered during a standard 3 hour treatment is generally about 50–100 mg. Such large amounts are apparently required for two reasons: first, to counterbalance the effects of rapid clearance of t-PA from the circulation by hepatic cells (Krause, J., *Fibrinolysis*, 2:133–142 (1988)), and second, to overcome the effects of comparatively high concentrations of serine protease inhibitors that are present in plasma and platelets (Carrell, R. W. et al, *In: Proteinase Inhibitors*, Ed. Barrett, A. J. et al, Elsevier, Amsterdam, pages 403–420 (1986)).

The major physiological inhibitor of t-PA is the serpin, PAI-1, a glycoprotein of approximately 50 kd (Pannekoek, H. et al, *EMBO J.*, 5:2539–2544 (1986); Ginsberg, D. et al, *J. Clin. Invest.*, 78:1673–1680 (1980); and Carrell, R. W. et al, *In: Proteinase Inhibitors*, Ed. Barrett, A. J. et al, Elsevier, Amsterdam, pages 403–420 (1986) ). PAI-1 has been implicated as the cause of reduced fibrinolytic capacity of plasma from survivors of myocardial infarctions (Hamsten, A. et al, *New Eng. J. Med.*, 313:1557–1563 (1985)). In addition, PAI-1 is an acute phase reactant and the elevated levels associated with myocardial infarction may attenuate the fibrinolytic activity of substantial amounts of the t-PA remaining in the plasma after therapeutic infusion of the t-PA (Lucore, C. L. et al, *Circ.*, 77:660–669 (1988)). The second-order rate constant for association of PAI-1 with t-PA is extremely high (Hekman, C. et al, *Arch. Biochem. Biophys.*, 262:199–210 (1988)) and accounts for the initial, "fast-phase" inhibition of t-PA by human plasma (Colucci, M. et al, *J. Lab. Clin. Med.*, 108:53–59 (1986)). The rapid neutralization of t-PA by PAI-1 in vivo, may therefore contribute to coronary restenosis after thrombolytic therapy, a complication that affects between 10% and 35% of patients treated for acute myocardial infarction (Chesebro, J. H. et al, *Circ.*, 76:142–154 (1987)).

Although the association constants of other serpins, such as Cl esterase inhibitor and alpha-2-antiplasmin, with t-PA are orders of magnitude lower than that of PAI-1 (Ranby, M. et al, *Throm. Res.*, 27:175–183 (1982); and Hekman, C. et al, *Arch. Biochem. Biophys.*, 262:199–210 (1988)), these serpins nevertheless bind to infused t-PA (Lucore, C. L. et al, *Circ.*, 77:660–669 (1988)) and may attenuate the beneficial pharmacological properties of t-PA.

Besides t-PA and PAI-1, many other serine protease-serpin pairs are of great medical importance. For example u-PA, like t-PA, is useful in the treatment of myocardial infarction and is subject to inhibition by the same serine protease inhibitors as t-PA.

Thrombin, the serine protease used topically to promote blood clotting of wounds, is a procoagulant. Its cognate serpin, antithrombin III, is an anti-coagulant that specifically inhibits a number of serine proteases that participate in the blood coagulation cascade, including thrombin and Factors IXa, Xa, XIa and XIIa (Heimburger, N. et al, *In: Proceed-* ings of the International Research Conference on Proteinase Inhibitors, Ed. Fritz, H. et al, Walter de Gruyter, New York, pages 1–22 (1971); Kurachi, K. et al, Biochem., 15:373–377 (1976); Kurachi, K. et al, Biochem., 16:5831–5839 (1977); and Osterud, B. et al, Semin. Thromb. Haemost., 35:295–305 (1976)). Antithrombin III has been used therapeutically to treat disseminated intravascular coagulation. The activation of protein C by thrombin results in the self-limitation of the blood coagulation process because activated protein C inactivates coagulation factors Va and VIIIa, and is itself inhibited by its cognate serpin, protein C inhibitor.

Kallikrein, which functions to induce uterine contraction, to increase vascular permeability, and to initiate the intrinsic pathway of blood coagulation, is subject to inhibition by the serpin alpha-1-antitrypsin, one of the more important serpins.

Alpha-1-antitrypsin also inhibits leukocyte elastase and cathepsin, as well as trypsin, chymotrypsin and plasmin Heimburger, N. et al, In: Proceedings of the International Research Conference on Proteinase Inhibitors, Ed. Fritz, H. et al, Walter de Gruyter, New York, pages 1–47 (1971); Janoff, A., Am. Rev. Rasp. Dis., 105:121–127 (1972); and Ohlsson, K. et al, Eur. J. Biochem., 36:473–481 (1973)). The genetic deficiency of alpha-1-antitrypsin is directly related to emphysema (Carrell, R. W. et al, Trends Biochem. Sci., 10:20–24 (1985)) and alpha-1-antitrypsin replacement therapy has been used to treat emphysema (Marx, J. L., Science, 243:315–316 (1989)).

SUMMARY OF THE INVENTION

Accordingly, an object of the present invention is to improve wild-type serine proteases of the chymotrypsin superfamily, and in particular wild-type t-PA, by protein engineering, so as to increase their enzymatic efficiency and/or to alter the dosage thereof required without necessarily altering other beneficial pharmacological properties.

Another object of the present invention is to provide genes encoding the improved serine proteases of the chymotrypsin superfamily.

Still another object of the present invention is to alter wild-type serine protease inhibitors, particularly those of the serpin family, and in particular, wild-type PAI-1, so as to increase their inhibitory efficiency and/or to alter the dosage thereof required and render them capable of inhibiting the mutant serine proteases of the present invention.

Yet another object of the present invention is to provide genes encoding the improved serine protease inhibitors.

These and other objects of the present invention, which will be apparent from the detailed description of the present invention provided hereinafter, have been met by serine protease mutants of the chymotrypsin superfamily which are resistant to inhibition by their cognate inhibitors and genes encoding the same; and by serine protease inhibitor mutants that inhibit the serine protease inhibitor-resistant serine proteases; and genes encoding the same.

BRIEF DESCRIPTION OF THE DRAWINGS

FIG. 1 shows a comparison of the sequences of various serine proteases of the chymotrypsin superfamily. The sequences are aligned so as to demonstrate overlap of conserved amino acids. The numbers above trypsin refer to the numbering system used in the PDB3ptp.ent entry in the Protein Data Bank. The numbers above t-PA refer to the amino acids in the mature t-PA molecule.

FIGS. 2A–2F show a comparison of the sequences of various members of the serpin family of serine protease inhibitors. The sequences are aligned so as to demonstrate overlap of conserved amino acids. The numbers below alpha-1-antitrypsin and the numbers above PAI-1 refer to amino acid residues in the mature molecules.

FIGS. 3A–3C schematically illustrate the construction of the vectors employed to mutate and express the wild-type t-PA and the serpin-resistant mutants of t-PA of the present invention.

FIG. 4 shows a comparison of the activities of wild-type t-PA and serpin-resistant mutants of t-PA in an indirect chromogenic assay. In FIG. 4, ■ represents wild-type t-PA, ○ represents t-pA($R_{304}$→S), □ represents t-PA($R_{304}$→E), and ● represents t-PA($Del_{296}$-302).

FIG. 5 shows the effect of PAI-1 on the activities of wild-type t-PA and serpin-resistant mutants of t-PA in an indirect chromogenic assay. In FIG. 5, ■ represents wild-type t-PA, ○ represents t-pA($R_{304}$→S), □ represents t-PA($R_{304}$→E), and ● represents t-PA(Del296-302).

FIG. 6 shows a comparison of the activities of wild-type t-PA and serpin-resistant mutants of t-PA in an indirect chromogenic assay. In FIG. 6, □ represents t-PA($H_{297}$→Y), ● represents wild-type t-PA, + represents t-PA($K_{296}$→E), □ represents the triple mutant t-PA($K_{296}$, $R_{298}$, $R_{299}$→E, E, E), ▲ represents t-PA($R_{299}$→E), Δ represents t-PA($R_{298}$→E) and ○ represents t-PA($P_{301}$→G).

FIG. 7 shows the effect of PAI-1 on the activities of wild-type t-PA and serpin-resistant mutants of t-PA in an indirect chromogenic assay. In FIG. 7, □ represents t-PA($H_{297}$→Y), ● represents wild type t-PA, + represents t-PA($K_{296}$→E), ■ represents t-PA($K_{296}$, $R_{298}$, $R_{299}$→E, E, E), ▲ represents t-PA($R_{299}$→E), Δ represents t-PA($R_{298}$→E) and ○ represents t-PA($P_{301}$→G).

FIG. 8 schematically illustrates the construction of the vectors employed to mutagenize and express the wild-type PAI-1 and the mutants of PAI-1 of the present invention.

DETAILED DESCRIPTION OF THE INVENTION

As discussed above, the above-described objects of the present invention have been met in one embodiment by serine protease mutants of the chymotrypsin superfamily that are resistant to inhibition by their cognate inhibitor; and genes encoding the same.

In another embodiment of the present invention, the above-described objects have been met by serine protease inhibitor mutants that inhibit the serine protease inhibitor-resistant serine proteases of the present invention; and genes encoding the same.

In still another embodiment, the serine protease inhibitor mutants of the present invention also inhibit the wild-type serine protease of the chymotrypsin superfamily.

The particular serine protease of the chymotrypsin superfamily employed in the present invention is not critical thereto as all members of this serine protease sub-sub class of endopeptidases are homologous proteins that share a common mechanism of action. Specific examples of such serine proteases of the chymotrypsin superfamily include those listed above, i.e., t-PA, trypsin, trypsin-like protease, chymotrypsin, plasmin, elastase, u-PA, acrosin, activated protein C, Cl esterase, cathepsin G, chymase and proteases of the blood coagulation cascade including kallikrein, thrombin, and Factors VIIa, IXa, Xa, XIa and XIIa. The preferred serine protease of the chymotrypsin superfamily employed in the present invention is t-PA.

The particular serine protease inhibitor to which the mutant serine protease of the chymotrypsin superfamily is resistant to inhibition, is not critical to the present invention. Examples of such inhibitors include members of the BPTI family, the Kazal family, the SSI family, the serpin family, the soybean trypsin inhibitor (Kunitz) family, the potato inhibitor family, and the Bowman-Birk family.

The particular BPTI inhibitor to which the mutant serine protease of the chymotrypsin superfamily is resistant to inhibition, is not critical to the present invention. Examples of such BPTI inhibitors include BPTI, snake venom inhibitor, inter-alpha inhibitor, and the A4 amyloid precursor A4695.

The particular Kazal inhibitor to which the mutant serine protease of the chymotrypsin superfamily is resistant to inhibition, is not critical to the present invention. Examples of such Kazal inhibitors include pancreatic secretory inhibitor, ovomucoid and seminal plasma acrosin inhibitor.

The particular serpin inhibitor to which the mutant serine protease of the chymotrypsin superfamily is resistant to inhibition, is not critical to the present invention. Examples of such serpin inhibitors include PAI-1, PAI-2, PAI-3, Cl esterase inhibitor (Clinh), protein C inhibitor (PCinh), heparin cofactor II (HCII), alpha-2-antiplasmin (A2AP), antithrombin III (ATIII), alpha-1-antitrypsin (A1AT), protease nexin I (Nex-1), contrapsin (Cntrps), growth hormone regulated protein (GHRP), and alpha-1-antichymotrypsin (AChym). The preferred serpin, to which the serine protease of the chymotrypsin superfamily is resistant to inhibition, is PAI-1.

The particular serine protease inhibitor, from which the mutant serine protease inhibitor capable of inhibiting the serine protease inhibitor-resistant serine proteases of the chymotrypsin superfamily of the present invention is derived, is not critical to the present invention. Examples of such serine protease inhibitors include members of the BPTI, Kazal, SSI, Kunitz, potato inhibitors, Bowmam-Birk and serpin families, preferably serine protease inhibitors of the serpin family such as PAI-1, PAI-2, PAI-3, Cl esterase inhibitor, protein C inhibitor, heparin cofactor II, alpha-2-antiplasmin, antithrombin III, alpha-1-antitrypsin, protease nexin I, contrapsin, growth hormone regulated protein, and alpha-1-antichymotrypsin. The preferred mutant serpin that will inhibit the serine protease inhibitor-resistant serine proteases of the chymotrypsin superfamily is PAI-1.

All known serine protease inhibitors are structurally homologous in their reactive center loop and form similar interactions with their cognate serine proteases (Read, R. J. et al, *In: Proteinase Inhibitors*, Ed. Barrett, A. J. et al, Elsevier, Amsterdam, pages 301–336 (1986)). The structural correspondences between serine proteases and serine protease inhibitors can be used to build models of complexes that have not been studied heretofor.

Because of the high degree of structural homology between the catalytic domain of t-PA and other serine proteases (Blundell, T. et al, *Nature*, 326:347–352 (1987)), it was postulated in the present invention that the known structure of the complex between trypsin and BPTI (Huber, R. et al, *J. Mol. Biol.*, 89:73–101 (1974)); and Bode, W. et al, *In: Proteolysis and Physiological Regulation*, Academic Press, New York, pages 43–76 (1976)) might serve as a model for the interaction between t-PA and PAI-1. Other than the amino acids in the major recognition site, the amino acids of trypsin that make direct contact with BPTI are located in two separate regions of the polypeptide chain (residues 37–41 and 210–213) (see FIG. 1).

The region around amino acid residues $_{214}SWGS_{217}$ is highly conserved among all members of the chymotrypsin superfamily. By contrast, the region around amino acid residues $_{36}NSGYHF_{41}$ is more variable and forms part of the surface that interacts with the inhibitor. As shown in FIG. 1, the amino acid sequence of t-PA in this region differs from that of trypsin in two major respects. First, the Tyr ($Y_{39}$) residue of trypsin has been replaced with an Arg ($R_{304}$) residue in t-PA. Modelling based on the assumption that the interaction between t-PA and PAI-1 mimics that between trypsin and BPTI suggests that $R_{304}$ of t-PA can form a salt bridge with a Glu ($E_{350}$) residue of PAI-1. This Glu residue in PAI-1 is equivalent in position to $I_{19}$ of BPTI (Table VII below) which forms a van der Waal's contact with $Y_{39}$ of trypsin (Huber, R. et al, *J. Mol. Biol.*, 89:73–101 (1974)); and Bode, W. et al, *In: Proteolysis Physiological Regulation*, Academic Press, New York, pages 43–76 (1976)). Therefore, $E_{350}$ of PAI-1 is predicted to form an ion pair with $R_{304}$ of t-PA.

TABLE VII

|  | P1 | | P4' |
|---|---|---|---|
|  | 12 | . | 24 |
| BPTI | | GPCKARIIRYFYIN | |
|  | 343 | . . | 355 |
| PAI-1 | | VSARMAPEEIIMD | |
|  | 557 | . . | 569 |
| PLG | | CPGRVVGGCVAHP | |

Second, t-PA carries an additional stretch of seven amino acids ($_{296}KHRRSPG_{302}$, see FIG. 1) located adjacent to predicted contact between t-PA($R_{304}$) and PAI-1($E_{350}$). Four out of seven of these amino acids are positively-charged, while the predicted complementary region of PAI-1($_{350}EEI$-$IMD_{355}$) contains three negatively-charged residues. It was believed in the present invention that electrostatic interactions between these regions may play an important role in the formation or stabilization of complexes between t-PA and PAI-1. By contrast, such interactions could not occur when t-PA interacts with its substrate, plasminogen (PLG), which has no negatively-charged residues in the equivalent region (see Table VII above).

Comparisons of sequences of various serine proteases of the chymotrypsin superfamily, such as those shown in FIG. 1, can be used as a guide to design one or more mutations in the various serine proteases of the chymotrypsin superfamily so as to make them resistant to inhibition by their cognate wild-type inhibitors. Like t-PA, the other serine proteases of the chymotrypsin superfamily shown in FIG. 1 differ from trypsin at the important contact residue ($Y_{39}$ of trypsin) and in containing insertions of variable size located adjacent to the contact residue. Thus, examples of candidates for mutation include:

(i) amino acid residues that, in other serine proteases, occupy the position equivalent to that of Tyr ($Y_{39}$) of trypsin (the residue that forms a contact with Ile ($I_{19}$) of BPTI and therefore plays an important role in the interaction between the two proteins). In plasmin for example, a Met (M) residue occupies the position equivalent to $Y_{39}$ of trypsin. Mutation of this Met residue to another amino acid with different properties, such as charge or size (Glu (E) for example) is expected to eliminate or reduce the susceptibility of plasmin to inactivation by antiplasmin, although the particular substitute amino acid employed is not critical to the present invention. Similarly, mutation of the Gln (Q)

residue of thrombin (that occupies the position equivalent to $Y_{39}$ of trypsin) to another amino acid with different properties, such as charge or size (for example Asp (D)) is expected to eliminate or reduce the susceptibility of thrombin to inactivation by antithrombin III, although the particular substitute amino acid employed is not critical to the present invention; and (ii) residues of other serine proteases of the chymotrypsin superfamily that are not present in trypsin and map near the active site as small insertions on the surface of the molecule (see FIG. 1). For example plasmin contains an insert of 2 amino acids (RF) adjacent to the contact residue in a position equivalent to that occupied by $_{296}$KHRRSPG$_{302}$ of t-PA. Mutation by deletion or substitution of either or both of these two amino acids, or by insertion of small numbers of additional amino acids is expected to eliminate or reduce the interaction with the inhibitor without necessarily affecting the catalytic site of the serine protease. As another example, u-PA contains an insert of six amino acids (RHRGGS) adjacent to the contact residue in position equivalent to that occupied by $_{296}$KHRRSPG$_{302}$ of t-PA. Mutation or deletion of these six residues is expected to reduce or eliminate the interaction with serine protease inhibitors in a manner similar to that observed for the mutant t-PA(Del$_{296}$-302).

Similarly, the region of the serine protease inhibitors within the reactive center is quite variable and forms part of the surface that interacts with the serine protease. Comparisons of sequences of various serine protease inhibitors of the serpin family, such as those shown in FIGS. 2A–2F, can be used as a guide to design one or more mutations in the various serine protease inhibitors, and in particular, in members of the serpin family of serine protease inhibitors, so as to make them able to efficiently inhibit the serine protease inhibitor-resistant serine proteases of the chymotrypsin superfamily of the present invention. Like PAI-1, other serpin family members shown in FIG. 2A–2F differ in sequence in the important contact amino acid residues ($E_{350}$ of PAI-1) and contain insertions of variable size located adjacent to the contact residue (see Table VIII below).

Thus, examples of candidates for mutation include:

(i) amino acid residues that, in other serine protease inhibitors, occupy the position ($P_4'$) equivalent to that of Glu($E_{350}$) of PAI-1 (the residue that forms a contact with Arg($R_{304}$) of t-PA and therefore plays an important role in the interaction of the two proteins). In the present invention, the Glu residue of PAI-1($E_{350}$) has been mutated to Arg (R) in order to restore the electrostatic interaction which was disrupted by construction of the $R_{304} \rightarrow E$ mutation in t-PA. This specific mutation in the serpin has been constructed so as to be complementary to the mutation that was introduced in the serine protease which renders it resistant to inhibition by the wild-type serpin. This complementary $E_{350} \rightarrow R$ mutation in the serpin was specifically chosen to render the serpin capable of inhibiting the serine protease inhibitor-resistant serine proteases of the chymotrypsin superfamily of the present invention; however, the particular substitute amino acid employed is not critical to the present invention. For example, if the Met (M) residue in plasmin equivalent to $Y_{39}$ of trypsin (see FIG. 1) were altered to another amino acid with different properties, such as charge or size (as the example given above, Glu (E)), and that mutant plasmin showed reduced susceptibility to inhibition by wild-type alpha-2-antiplasmin, then mutation of the $P_4'$ Ser (S) residue in alpha 2-antiplasmin, to another amino acid (Arg (R) for example) capable of interacting with the altered Glu residue in plasmin, is expected to restore the susceptibility of the mutant plasmin to inactivation by the mutant alpha-2-antiplasmin. Similarly, if the Gln (Q) residue of thrombin were altered to Asp (D), as in the example for mutation of thrombin given above, then mutation of the P6' Arg (R) residue of antithrombin III to Glu (E) is expected to restore susceptibility of the wild-type inhibitor-resistant thrombin to inhibition by the mutant anti-thrombin III; and (ii) additional amino acid residues of other members of the various families of serine protease inhibitors within the reactive center that form part of the interaction surface with their cognate serine protease. These residues are shown in Table VIII above for the serpin family of serine protease inhibitors.

For example, alpha-2-antiplasmin contains the sequence SLSSFSVN in the reactive center in a position equivalent to the $_{348}$APEEIIMD$_{355}$ of PAI-1. Mutation by substitution of any of these eight amino acids or by insertion of small numbers of additional amino acids is expected to restore the interaction with the serine protease provided that those substitutions or insertions are complementary in some prop-

TABLE VIII

| Serpin | 344 | | P1–P1' | | | | | | | | | | | | | | | | 358 |
|---|---|---|---|---|---|---|---|---|---|---|---|---|---|---|---|---|---|---|---|
| h PAI-1 | S | A | – | R | M | A | P | E | E | – | – | – | – | – | I | I | M | D | R | P | F |
| r PAI-1 | S | A | – | R | M | A | P | T | E | – | – | – | – | – | M | V | L | D | R | S | F |
| h PAI-2 | T | G | – | R | T | G | H | G | G | – | – | – | P | Q | F | V | A | D | H | P | F |
| h A1AT | I | P | – | M | S | I | P | P | E | – | – | – | – | – | V | K | F | N | K | P | F |
| b A1AT | I | P | – | M | S | I | P | P | E | – | – | – | – | – | V | K | F | N | K | P | F |
| m A1AT | V | P | – | Y | S | M | P | P | I | – | – | – | – | – | L | R | F | D | H | P | F |
| r GHRP | L | – | – | K | S | L | P | Q | T | I | – | – | P | L | L | N | F | N | R | P | F |
| h AChym | T | L | – | L | S | A | L | V | E | T | R | T | I | – | V | R | F | N | R | P | F |
| m Cntrps | G | I | R | K | A | I | L | P | A | – | – | – | – | – | V | H | F | N | R | P | F |
| h ATIII | A | G | – | R | S | L | N | P | N | – | – | R | V | T | F | K | A | N | R | P | F |
| h HCII | M | P | – | L | S | T | Q | V | R | – | – | – | – | – | F | T | V | D | R | P | F |
| h A2AP | S | – | – | R | M | S | L | S | S | – | – | – | – | – | F | S | V | N | R | P | F |
| h C1inh | A | A | – | R | T | L | L | V | – | – | – | – | – | – | F | E | V | Q | Q | P | F |
| h PCinh | T | F | – | R | S | A | R | L | N | – | – | S | Q | R | L | V | F | N | R | P | F |
| r Nex-1 | A | – | – | R | S | S | P | P | W | – | – | – | – | – | F | I | V | D | R | P | F |

(h = human; r = rat; b = baboon; and m = mouse)

erty, such as charge or size or hydrophobicity, to the amino acid residues that were introduced into the serine protease, which originally rendered it resistant to the wild-type serpin.

The mutant serine proteases and mutant serine protease inhibitors of the present invention may be point mutants, deletion mutants, addition mutants, or mutants containing combinations of these types of mutations.

The mutant serine proteases and mutant serine protease inhibitors of the present invention can be prepared, e.g., by the well known techniques of oligonucleotide-mediated mutagenesis (Zoller, M. et al, *DNA*, 3:479–488 (1984); Kunkel, T. et al, *Proc. Natl. Acad. Sci. USA*, 82:488–492 (1985); and Kunkel, T. et al, *Current Protocols in Molecular Biology*, Green Publishing Associates & Wiley Interscience, New York (1987)). However, the precise method of preparing the mutation in the serine protease or serine protease inhibitor is not critical to the present invention.

The mutant serine proteases of the present invention can be screened for those having the desired properties, i.e., serine protease activity yet resistance to inhibition by the cognate inhibitor, using well known assays, such as described in Lottenberg, R. et al, *Meth. Enzymol.*, 80:341–361 (1981).

The mutant serine protease inhibitors of the present invention can be screened for those having the desired properties, i.e., serine protease inhibitor activity against the serine protease inhibitor-resistant serine proteases of the present invention, using well-known assays, such as described in Lottenberg, R. et al, *Meth. Enzymol.*, 80:341–361 (1–981); Holmes, W. E. et al, *Biochem.*, 26:5133–5140 (1987); and Hekman, C. M. et al, *Arch. Biochem. Biophys.*, 262:199–210 (1988).

The work described herein demonstrates for the first time that it is possible to modify serine proteases by mutagenesis so as to reduce or eliminate the interaction between serine proteases of the chymotrypsin superfamily and their cognate inhibitors. This allowls the mutant serine proteases to remain enzymatically more active than the wild-type enzyme in the presence of the cognate inhibitors, with the amount of residual activity depending on the degree to which their interaction with their cognate inhibitor is inhibited. The administration of such mutated serine proteases is believed to be of benefit in a variety of clinical and commercial applications. For example, a mutated form of activated protein C is believed to be useful when it would be advantageous to inhibit the coagulation of blood, just as the mutated forms of t-PA described in Example 1 herein are believed to be useful to extend the effective life of t-PA in the circulation of a patient with a thrombotic disorder where extended fibrinolysis is required.

The work described herein also demonstrates for the first time that it is possible to modify serine protease inhibitors mutagenesis so as to functionally restore the interaction between serine protease inhibitor-resistant mutant serine proteases of the chymotrypsin superfamily and their cognate serine protease inhibitors by suitably altering the structure of the serine protease inhibitor. This allows the mutant serine proteases to be inactivated more rapidly than they would be in the presence of the cognate wild-type serine protease inhibitor, with the rate of inhibition depending on the degree to which their interaction with the mutant serine protease has been restored. The administration of such mutant serine protease inhibitors is believed to be of benefit in a variety of clinical and commercial applications to limit the activity of serine protease inhibitor-resistant serine proteases. For example, a mutated form of protein C inhibitor is believed to be useful when it would be advantageous to promote the coagulation of blood in the presence of a mutant form of activated protein C. Similarly, the mutated forms of PAI-1 are believed to be useful in shortening the effective life of serine protease inhibitor-resistant t-PA, e.g. t-PA($R_{304}$→E), in the circulation of a patient treated for a thrombotic disorder should an invasive procedure be required. Such altered serine protease inhibitors could thus be used as antidotes for the serine protease inhibitor-resistant serine proteases.

The amount of mutant serine protease of the present invention to be administered in clinical applications will depend upon the particular mutant serine protease employed, the desired therapeutic effect of the serine protease, and on factors such as the sex, age, weight and physiological condition of the patient to whom the protease is to be administered. The amount of mutant serine protease to employ can be determined by routine experimentation.

The amount of mutant serine protease inhibitor of the present invention to be administered in clinical applications will depend upon the particular mutant serine protease inhibitor employed, the desired therapeutic effect of the serine protease inhibitor, and on factors such as the sex, age, weight and physiological condition of the patient to whom the serine protease inhibitor is to be administered. The amount of mutant serine protease inhibitor to employ can be determined by routine experimentation.

The mutant t-PAs of the present invention should be administered as determined by tests in appropriate in vitro and in vivo models and in clinical trials. It is anticipated that the doses required will be between 10 and 1000-fold less than that which is required for wild-type t-PA.

The mutant PAI-1s of the present invention should also be administered as determined by tests in appropriate in vitro and in vivo models and in clinical trials. It is anticipated that the doses required will be approximately the same as those required for the mutant t-PAs.

The mutant serine proteases of the present invention can be administered with any pharmaceutically acceptable carrier or diluent as is well known in the art, such as a physiological saline solution (Lucore, C. L. et al, *Circ.*, 77:660–669 (1988); and Chesebro, J. H. et al, *Circ.*, 76:142–154 (1987)).

The mutant serine protease inhibitors of the present invention can also be administered with any pharmaceutically acceptable carrier or diluent as is well known in the art, such as a physiological saline solution (Lucore, C. L. et al, *Circ.*, 77:660–669 (1988); and Chesebro, J. H. et al, *Circ.*, 76:142–154 (1987)).

The particular mode of administration of the mutant serine proteases of the present invention is dependent on the particular application thereof. Examples of such modes of administration include intravenous or intraperitoneal injection, intracoronary infusion, topical application and aerosol inhalation.

The particular mode of administration of the mutant serine protease inhibitors of the present invention is dependent on the particular application thereof. Examples of such modes of administration include intravenous or intraperitoneal injection, intracoronary infusion, topical application and aerosol inhalation.

The following examples are provided for illustrative purposes only and are in no way intended to limit the scope of the present invention.

EXAMPLE 1 t-PA MUTANTS

Although the technology described in this example is directed to the use of t-PA as the serine protease and PAI-1 as the cognate serine protease inhibitors, other serine proteases of the chymotrypsin superfamily, such as those described above, and their cognate inhibitors, such as those described above, could easily and readily be employed using the techniques described herein without departing from the spirit and scope of this invention.

A. Selection of t-PA Sites for Mutagenesis

To test the hypothesis that residues $Arg_{304}$ and ($_{296}$KHRRSPG$_{302}$) of t-PA interact with PAI-1, oligonucleotide-mediated mutagenesis was used to produce the three mutant forms of t-PA shown in Table IX below.

TABLE IX

| wild-type t-PA | FAKHRRSPGERFLC |
|---|---|
| t-PA(Arg$_{304}$→S) | FAKHRRSPGE SFLC |
| t-PA(Arg$_{304}$→E) | FAKHRRSPGE EFLC |
| t-PA(Del$_{296-302}$) | FA.......ERFLC |

Mutant t-PA(Del$_{296}$-302) lacks the seven amino acid insertion discussed above which is not found in trypsin, and was constructed so as to completely remove a portion of the t-PA sequence which interacts with the cognate serine protease inhibitor, PAI-1. Mutants t-PA(R$_{304}$→S) and t-PA(R$_{304}$→E) contain substitutions of Ser and Glu, respectively, for Arg$_{304}$, and were chosen to selectively alter the positively-charged Arg residue and eliminate its interaction with the cognate serine protease inhibitor, PAI-1. A variety of other substitutions can be made for R$_{304}$ which would produce a t-PA with reduced susceptibility to its cognate serine protease inhibitor due to a lack of charged-pair interaction. For example, point mutations that convert the positively-charged residues in the loop (residues 296-302) to negatively-charged or neutral amino acids would be predicted to prevent, reduce or destabilize the interaction between t-PA and PAI-1. A similar result can be obtained by replacing P$_{301}$ with another amino acid, with the exception of Gly (G). Additionally, insertion mutations can be made between residues 304 and 305, or anywhere between residues 296 and 305, so as to insert a series of about 1–6 amino acids that will not interact properly with the PAI-1 residues. Different substitutions and/or combinations of substitutions, insertions and deletions would be expected to affect the interaction between t-PA and PAI-1 to different extents, thereby allowing a variety of t-PAs to be generated with properties appropriate for particular applications or clinical conditions.

B. Oligonucleotide-mediated Mutagenesis of t-PA

Oligonucleotide-mediated mutagenesis of t-PA was carried out essentially as described by Zoller, M. et al, *DNA*, 3:479–488 (1984) as modified by Kunkel, T., *Proc. Natl. Acad. Sci. USA*, 82:488–492 (1985); and Kunkel, T. et al, *Current Protocols in Molecular Biology*, Green Publishing Associates & Wiley Interscience, New York (1987).

Figure 3B:
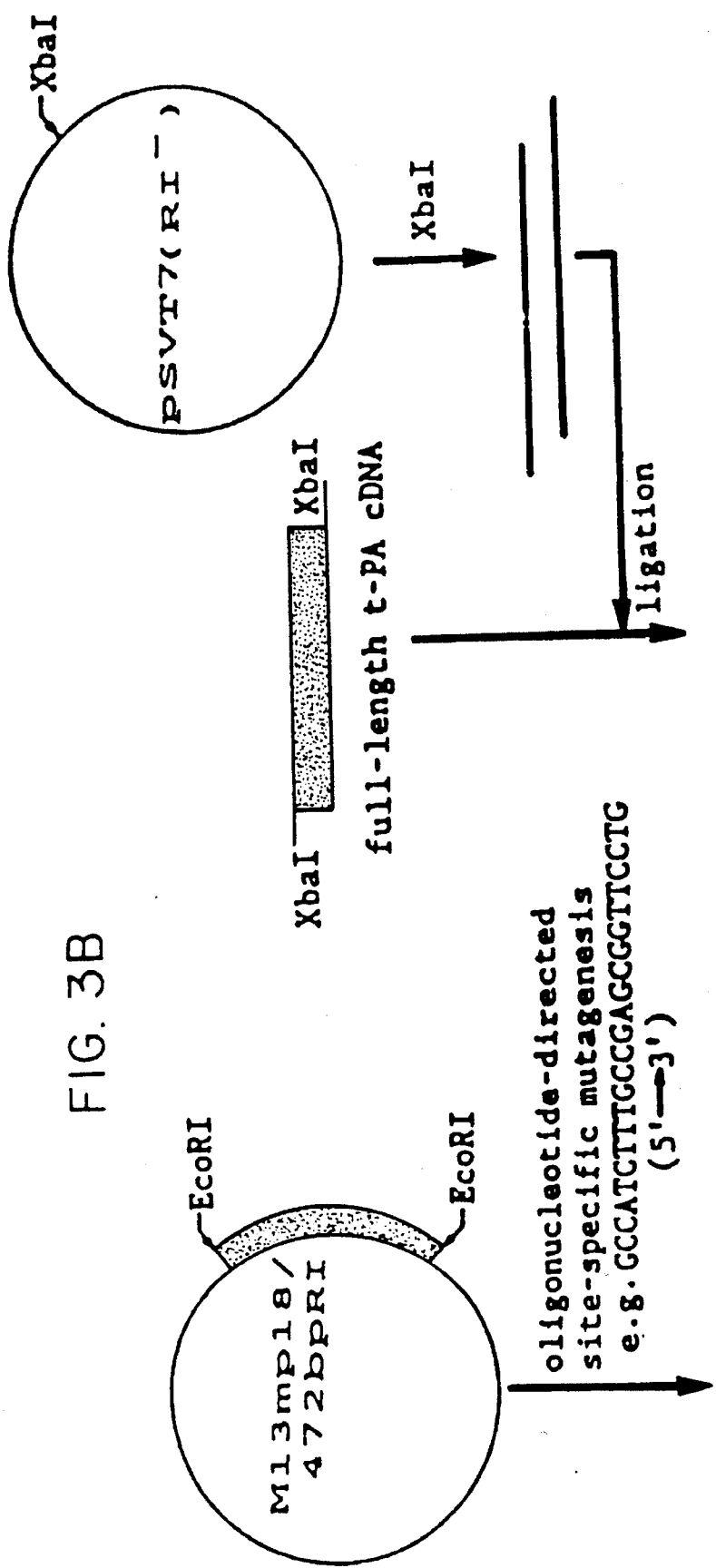
Figure 3C:
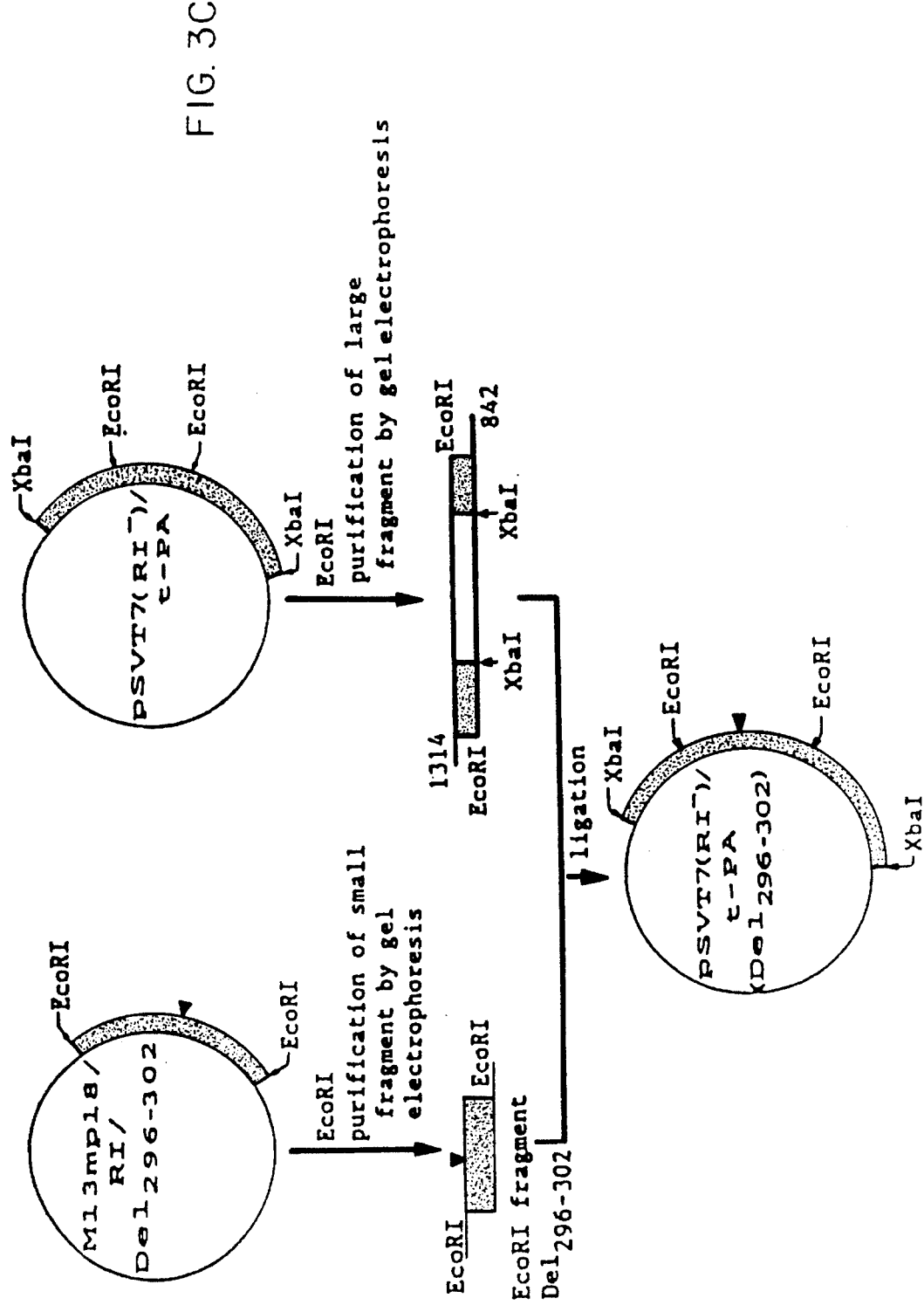

First, plasmid pSVT7(RI$^-$)/t-PA, which contains a cloned copy of the cDNA encoding full-length human t-PA, was prepared as described by Sambrook, J. et al, *Mol. Biol. Med.*, 3:459–481 (1986). pSVT7(RI$^-$)/t-PA is a derivative of pSVT7 (Bird, P. M. et al, *J. Cell Biol.*, 105:2905–2914 (1987)) (see FIG. 3).

pSVT7 was constructed from pKC3. pKC3 is a derivative of pko (Van Doren, K. et al, *J. Virol.*, 50:606–614 (1984)) in which the pBR322-derived sequences from the AvaI site to the EcoRI site (which contain the origin of replication and the β-lactamase gene) have been replaced by those of pUC 8 (Messing, J., *Meth. Enzymol.*, 101:20–78 (1983)). In addition, a polylinker has been inserted into the unique HindIII site and the PvuII site upstream of the SV40 origin has been converted into a ClaI site. Vector pSVT7 was obtained by inserting a 20 base pair fragment containing a bacteriophage T7 RNA polymerase-specific promoter (Pharmacia Fine Chemicals, Piscataway, N.J.) into the unique StuI site of pKC3. This StuI site lies within sequences derived from the early region of SV40 at nucleotide 5190 in the SV40 sequence and approximately 30 base pairs downstream from the point of initiation of the early transcript (Tooze, J. et al, *DNA Tumor Viruses*, Cold Spring Harbor Press, page 813 (1981)).

Then, the single EcoRI site was removed from pSVT7 by filling the recessed 3'-ends with the Klenow fragment of *E. coli* DNA polymerase. The resulting expression vector was designated pSVT7(RI$^-$) (see FIGS. 3A–3C).

Next, cDNA coding for wild-type t-PA was excised from plasmid pL611 (Sambrook, J. et al, *Mol. Biol. Med.*, 3:459–481 (1986); provided by Genetics Institute, Boston, Mass.) and inserted into pSVT7(RI$^-$). pL611 contains, immediately upstream from the initiating AUG codon of t-PA, a synthetic oligonucleotide that introduces cleavage sites for NcoI and BamHI. Approximately 280 base pairs downstream of the TGA termination codon, a BalI site lies within the 3' untranslated sequence of the t-PA cDNA. XbaI linkers were added to the approximately 1965 base pair NcoI-BalI fragment of t-PA DNA that was excised from plasmid pL611. This NcoI-BalI fragment contains the sequences that code for the complete t-PA protein but lacks sequences corresponding to (i) the distal 3'-untranslated region of t-PA mRNA and (ii) all of the 5'-untranslated sequences of t-PA mRNA, i.e., the sequences between a SalI site and the initiating ATG codon (Pennica, D. et al, *Nature*, 301:214–221 (1983)). The fragment of t-PA cDNA carrying XbaI sites at each end (Sambrook, J. et al, *Mol. Biol. Med.*, 3:459–481 (1986)) was used to generate pSVT7/t-PA (see FIGS. 3A–3C). The approximately 1970 base pair DNA fragment was excised from the resulting plasmid by digestion with XbaI, purified by 0.8% (w/v) agarose gel electrophoresis and inserted into the XbaI site of plasmid pSVT7(RI$^-$) so that the sequences coding for the N-terminus of t-PA were placed immediately downstream of the bacteriophage T7 and SV40 early promoters. The resulting plasmid was designated pSVT7(RI$^-$)/t-PA (see FIGS. 3A–3C).

Then, pSVT7(RI$^-$)/t-PA was digested to completion with EcoRI. The 472 base pair fragment (nucleotides 842–1314 which encodes the region covering amino acids 206 to 364) of t-PA was purified by 12% (w/v) agarose gel electrophoresis. This fragment was then ligated with replicative-form DNA of the bacteriophage M13 vector M13mp18 (Yanisch-Perron, C. et al, *Gene*, 33:103–119(1985)) which had previously been digested with EcoRI and dephosphorylated with calf intestinal alkaline phosphatase (see FIGS. 3A–3C).

Unless otherwise specified, these and other standard recombinant DNA procedures described herein were carried out as described in (i) Maniatis, T. et al, *Molecular Cloning: A Laboratory Manual*, 1st Edition, Cold Spring Harbor (1982) and (ii) *Meth. Enzymol.*, Volume 152, Ed. Berger, S. et al, Academic Press, New York (1987).

The ligated DNA was transfected into *E. coli* strain TG-1 (Gibson, T., Thesis, University of Cambridge, England (1984)). White plaques formed by recombinant bacteriophages were picked and the presence of the appropriate 472 base pair EcoRI fragment was verified by restriction mapping. Southern hybridization and DNA sequencing.

Mutations in the 472 base pair EcoRI fragment were introduced using a 5'-phosphorylated synthetic mutagenic primer as described by Kunkel, T. et al, *Proc. Natl. Acad.*

Sci. USA, 82:488–492 (1985); and Kunkel T., *Math. Enzymol.*, 154:367–382 (1987)). The sequences of the three mutagenic primers employed to construct the t-PA mutants were:

| | |
|---|---|
| t-PA($R_{304}$->S) | 5'GCCCGGAGAGTCGTTCCTGTGC3' |
| t-PA($R_{304}$->E) | 5'GCCCGGAGAGGAGTTCCTGTGC3' |
| t-PA($Del_{296-302}$) | 5'GCCATCTTTGCCGAGCGGTTCCTG3' |

The above protocol uses a DNA template, produced in a strain of *E. coli* that is dut⁻, ung⁻, i.e., strain CJ236 (Kunkel, T. et al, *Proc. Natl. Acad. Sci. USA*, 82:488–492 (1985); and Kunkel, T., *Meth. Enzymol.*, 154:367–382 (1987)). The DNA template contains a small number of uracil residues in place of thymine.

After the mutagenic primer was extended in vitro, the partially-filled circular DNA was transfected into a strain of *E. coli* that is dut⁺, ung⁺, i.e., TG-1 (Gibson, T., Thesis, University of Cambridge, England (1984)). The uracil residues in the template strand were then removed in vivo by the action of the enzyme uracil N-glycosylase. This generated lethal lesions in the template strand and therefore allowed rapid and efficient recovery of mutants.

More specifically, the uracil-containing template DNAs were annealed to the 5' phosphorylated mutagenic primers shown above. Extension of the primer was carried out for 12–16 hours at 15° C. using the Klenow fragment of *E. coli* DNA polymerase. The newly-synthesized strand was ligated to the 5' end of the mutagenic primer with bacteriophage T4 DNA ligase, forming a circle bearing a mismatch. The resulting DNA was used to transfect *E. coli* strain TG-1 (Gibson, T., Thesis, University of Cambridge, England (1984)) and single-stranded DNA was prepared from a number of the plaques. These DNAs were completely sequenced. The double-stranded replicative form of the DNAs of proven mutants was then isolated and the mutated 472 base pair fragments were isolated by digestion with EcoRI and electrophoresis through 1.2% (w/v) agarose gels. As described in detail below, these fragments containing mutations were then used to reconstruct versions of the t-PA cDNA that encoded the t-PA mutants of interest.

C. Construction of Expression Vectors for Mutant t-PAs

Mutants of t-PA in plasmid pSVT7(RI⁻)/t-PA were constructed as follows: The central 472 base pair EcoRI fragment of t-PA cDNA was removed from plasmid pSVT7(RI⁻)/t-PA by digestion with EcoRI and by 1.2% (w/v) agarose gel electrophoresis. The remaining linear fragment of the plasmid DNA was then ligated to the versions of the 472 base pair fragment created by oligonucleotide-mediated mutagenesis (see FIGS. 3A–3C). The resulting plasmids were designated pSVT7(RI⁻)/t-PA($R_{304}$->S), pSVT7(RI⁻)/t-PA($R_{304}$->E) and pSVT7(RI⁻)/t-PA($Del_{296}$-302).

*E. coli* strain DH-1 (Hanahan, D. et al, *DNA Cloning*, Volume 1, Ed. Glover, D. M., I.R.L. Press, Oxford, pages 109–135 (1985)) was transformed with the above mutant plasmids and the resulting strains were designated pSVT7(RI⁻)/t-PA($R_{304}$->S) [DH-1]; pSVT7(RI⁻)/t-PA($R_{304}$->E) [DH-1]; and pSVT7(RI⁻)/t-PA($Del_{296}$-302) [DH-1], respectively. The presence of the correct fragment was confirmed by hybridization to the appropriate radiolabeled mutagenic oligonucleotide and the orientation of the fragment was verified by restriction mapping and DNA sequencing, using the appropriate mutagenic oligonucleotides as primers.

pSVT7(RI⁻)/t-PA($R_{304}$->S) [DH-1], pSVT7(RI⁻)/t-PA($R_{304}$->E) [DH-1] and pSVT7(RI⁻)/t-PA($Del_{296}$-302) [DH-1] have been deposited on Feb. 21, 1989 at the American Type Culture Collection, 12301 Parklawn Dr., Rockville, Md. 20852 under ATCC Nos. 67894, 67896 and 67895, respectively.

D. Transfection of COS Cells

Next, approximately $10^6$ COS cells (Gluzman, Y. et al, *Cell*, 23:175–182 (1981)) per 100 mm dish were transfected with 1.0 μg of the appropriate plasmid DNA purified by the alkaline lysis procedure (Maniatis, T. et al, *Molecular Cloning: A Laboratory Manual*, 1st edition, Cold Spring Harbor (1982)). More specifically, the medium was removed from the COS cells by aspiration and the monolayers were washed once with 5.0 ml of Dulbecco's medium (GIBCO, Inc.) containing 10 mM HEPES (pH 7.15) (Sigma Chemical Co.). After removal of the wash solution, the plasmid DNA was then added to the monolayers in a volume of 1.5 ml of wash solution containing 300 μg of DEAE-dextran (Pharmacia, Inc.). The monolayers were then incubated for 1 hour at 37° C. in an humidified atmosphere containing 6.0% $CO_2$. The monolayers were agitated gently every 20 minutes during this period. After the monolayers had been exposed to the plasmid DNA for 1 hour, they were washed once with Dulbecco's medium containing 10 mM HEPES (pH 7.15) and then 10 ml Dulbecco's medium containing 10% (v/v) fetal bovine serum (GIBCO, Inc.) and 100 μM chloroquine (Sigma Chemical Co.) was added. The monolayers were then incubated at 37° C. for 4 hours as described above, and washed twice with 5.0 ml of Dulbecco's medium lacking fetal bovine serum but containing 10 mM HEPES (pH 7.15). 10 ml of Dulbecco's medium containing 10% (v/v) fetal bovine serum was then added and the monolayers were incubated at 37° C. as described above for 12 hours. Then, the monolayers were washed three times each with 5.0 ml with Dulbecco's medium lacking fetal bovine serum and incubated at 37° C. in the same medium for a further 36–60 hours. Mock-transfected cells were treated identically except that plasmid DNA was omitted from the solution containing DEAE-dextran. At the end of the incubation period, the supernatant medium was collected from the cells and analyzed as described below.

E. Quantitation of Wild-Type and Mutant t-PAs by Solid-Phase Radioimmunoassay

A solid-phase radioimmunoassay was performed essentially as described for influenza hemagglutinin (Gething, M. J. et al, *Nature*, 293:620–625 (1981)) using the IgG fraction of rabbit antisera raised against purified human t-PA so as to quantitate the amounts of wild-type and mutant t-PAs produced in the COS cells. The concentration of t-PA determined by this method was between 0.5 and 1.0 μg/ml.

F. Enzymatic Assay of Wild-Type and Mutant t-PAs

An indirect chromogenic assay was carried out so as to determine the activities of the wild-type and mutant t-PAs produced in the COS cells. In this assay, free p-nitroaniline is released from the chromogenic substrate Spectrozyme PL (H-D-norleucylhexahydrotyrosyl-lysine-p-nitroanilide diacetate salt) (American Diagnostica, Inc.) by the action of plasmin generated by the action of t-PA on plasminogen. The release of free p-nitroaniline was measured spectrophotometrically at $OD_{405}$ nm.

More specifically, 100 μl reaction mixtures comprising 150–200 pg of the t-PA to be tested, 0.4 mM of Spectrozyme PL, 0.1 μM of Lys-plasminogen (American Diagnostica, Inc.) and 0.5–25 μg/ml of soluble fibrin (Des-A-fibrinogen) (American Diagnostica, Inc.) in a buffer comprising 50 mM Tris-HCl (pH 7.5), 0.1M NaCl, 1.0 mM EDTA and 0.01% (v/v) Tween 80 were incubated at 37° C. in 96-well, flat-bottomed microtiter plates (Costar, Inc.) and the $OD_{405}$nm was measured with a Bio-tek microplate reader (Model EL310) at 15 or 30 minute intervals over a 2 hour period. Aliquots of buffer or appropriately-diluted samples of medium from mock-transfected cells were analyzed as controls and the OD values obtained (<0.01 unit) were subtracted from the corresponding test values. Delta OD values were measured as the change in optical density between 30 minutes and 60 minutes, i.e., following the lag phase of the reaction and the complete conversion of single-chain t-PA to the two-chain form. Under the conditions used in the standard assay (0.1 µM of Lys-plasminogen and 25 µg/ml of Des-A-fibrinogen), soluble fibrin stimulated the activity of t-PA 20–40 fold. The results are shown in FIG. 4.

Figure 4:
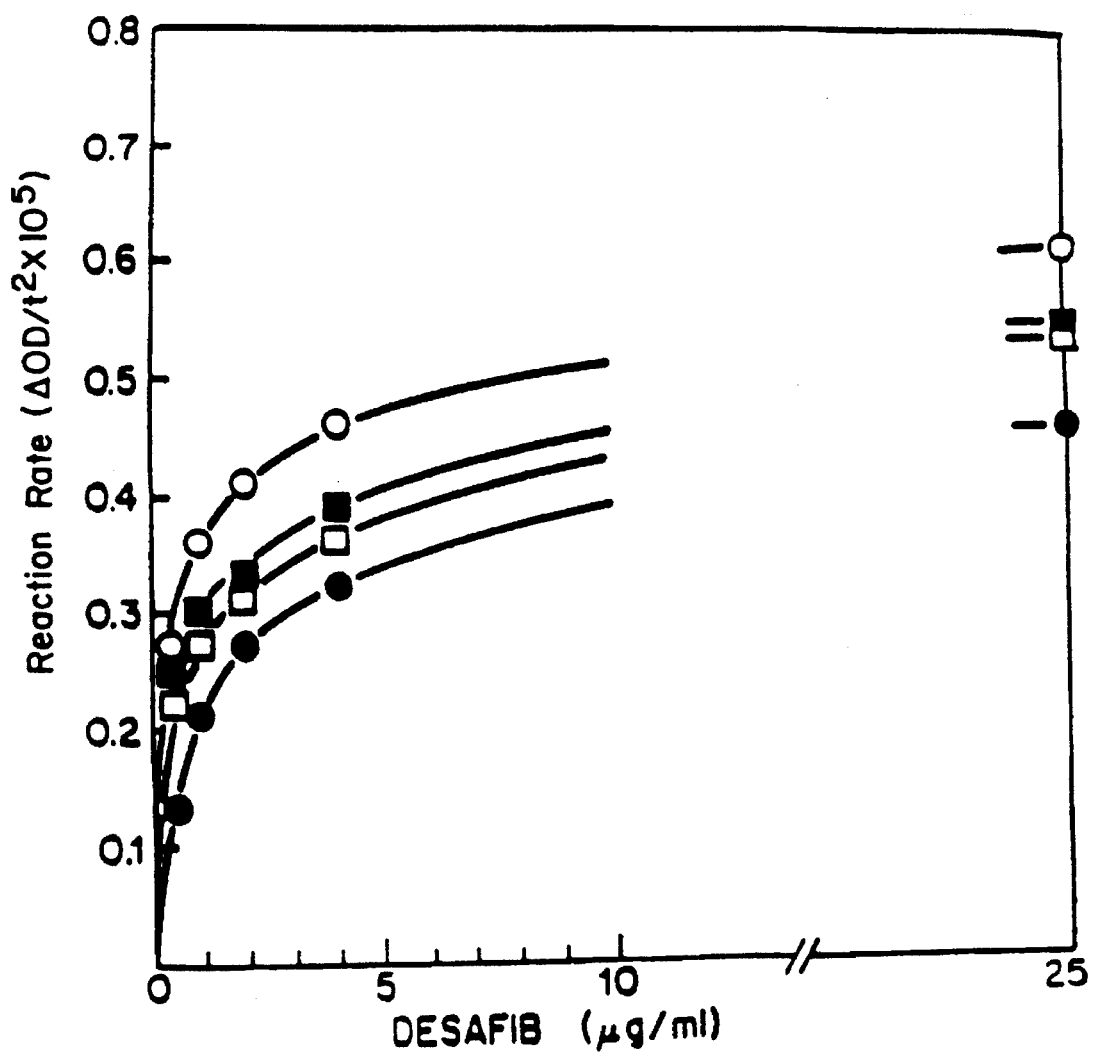

As shown in FIG. 4, all three of the above-described t-PA mutants of the present invention were found to be enzymatically active and their specific activities were not found to be significantly different from that of wild-type t-PA. In addition, the above-described t-PA mutants of the present invention were found to respond to varying concentrations of Des-A-fibrinogen in a manner similar to that of wild-type t-PA. The maximal stimulation by Des-A-fibrinogen was 20–40 fold. This is in agreement with the observations of others on wild-type t-PA using a Des-A-fibrinogen preparation (Karlan, B. et al, *Biochem. Biophys. Res. Comm.*, 142:147–154 (1987)). In each case, half-maximal stimulation occurred when Des-A-fibrinogen was present at a concentration of approximately 1.0 µg/ml.

Next, the $K_m$ and $K_{cat}$ values of the wild-type and mutant t-PAs were determined by assaying the various forms of the enzyme in the presence of saturating concentrations of Des-A-fibrinogen (25 µg/ml) and different concentrations (from 0.02–0.16 µM) of the substrate, Lys-plasminogen. The results are shown in Table X below.

TABLE X

| Enzyme | $K_m$ (µM) | $K_{cat}$ (s$^{-1}$) |
|---|---|---|
| Wild-type t-PA | 0.024 | 0.22 |
| t-PA($R_{304}\rightarrow$S) | 0.019 | 0.23 |
| t-PA($R_{304}\rightarrow$E) | 0.023 | 0.22 |
| t-PA(Del$_{296-302}$) | 0.029 | 0.17 |

As shown in Table X above, the $K_m$ and $K_{cat}$ values for the different t-PA mutants were similar to one another. The values are also similar to values for wild-type t-PA reported by Boose, J. et al, *Biochem.*, 28:635–643 (1989); and Hoylaerts, M. et al, *J. Biol. Chem.*, 257:2912–2919 (1982).

The data shown in FIG. 4 and Table X demonstrate that (i) deletion of amino acids 296–302 of t-PA and (ii) substitution of Ser or Glu for Arg at position 304 have little effect on the ability of t-PA to activate plasminogen and to be stimulated by soluble fibrin fragments.

To test whether deletion of amino acids 296–302 and substitution of Arg$_{304}$ affects the interaction of t-PA with PAI-1, approximately 250 pg (3.8 femtomoles) each of the wild-type and mutant t-PAs were pre-incubated for 20 minutes with 0–480 femtomoles of partially-purified recombinant PAI-1. The residual enzymatic activity was then measured using the indirect chromogenic assay described above. The partially-purified recombinant PAI-1 was obtained as described in Example 2 below. The results are shown in FIG. 5.

Figure 5:
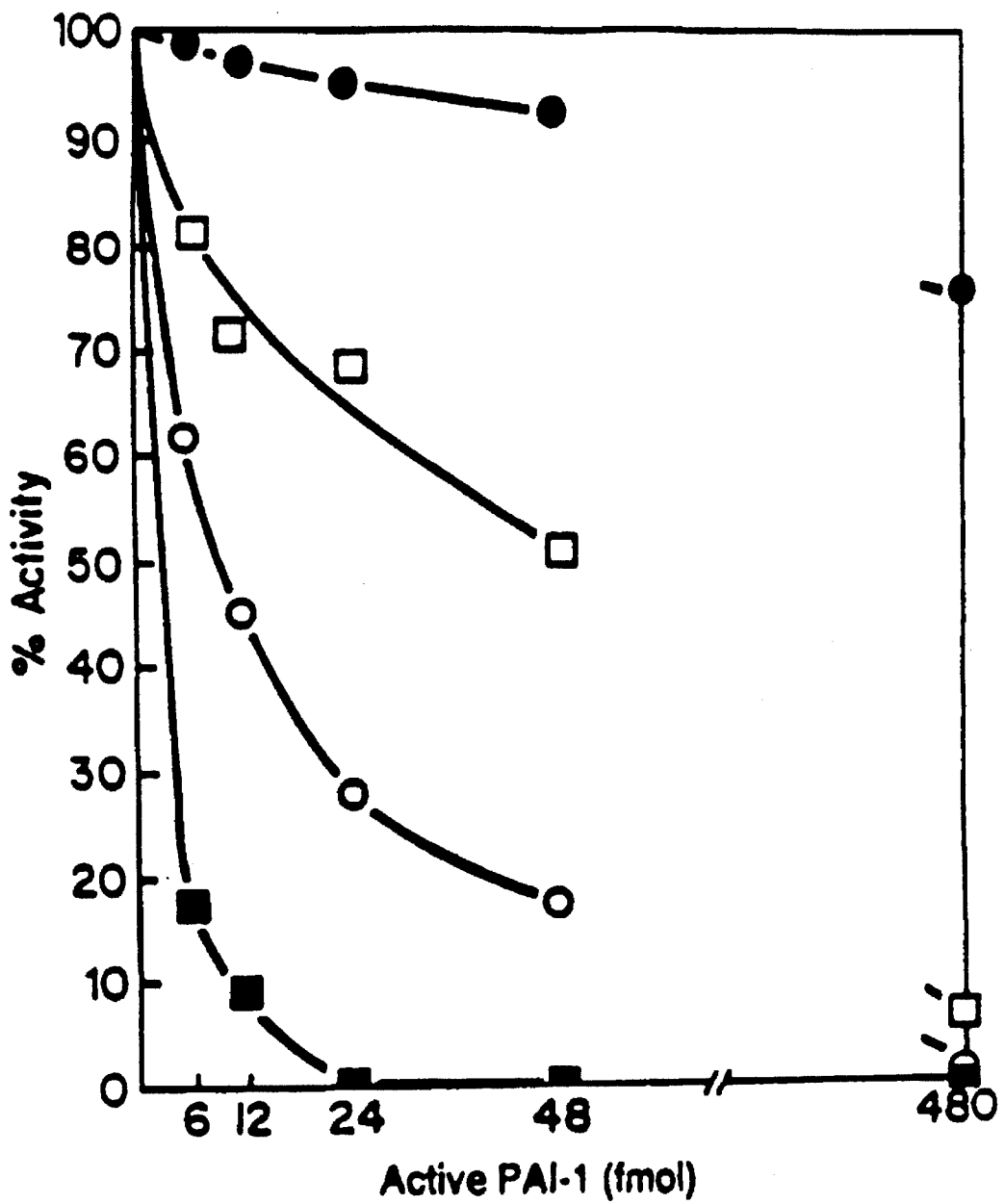

As shown in FIG. 5, all three of the t-PA mutants of the present invention behave quite differently from wild-type t-PA. That is, under conditions where wild-type t-PA (■) is completely inhibited by PAI-1 (24 femtomoles of PAI-1), the deletion mutant t-PA(Del$_{296}$-302) (●) retains approximately 95% of its activity. Only when high concentrations of PAI-1 are present (480 femtomoles of PAI-1), does mutant t-PA(Del$_{296}$-302) (●) display any significant diminution of enzymatic activity. The two substitution mutants, i.e., t-PA($R_{304}\rightarrow$S) (○) and t-PA($R_{304}\rightarrow$E) (□), also are resistant to inhibition by PAI-1, although to different extents. Also, as shown in FIG. 5, the two substitution mutants containing Ser or Glu instead of Arg require approximately 4 and 25 times more PAI-1, respectively, for half-maximal inhibition of enzyme activity than does wild-type t-PA.

The above data indicate that amino acids 296–302 and 304 are not involved in catalytic functions of t-PA, but play an important role in the interaction of the enzyme with its cognate serine protease inhibitor, PAI-1. Using the structure of trypsin as a model, these amino acids are predicted to map near the active site of the serine protease, some distance from the catalytic triad. Thus, the area of contact between t-PA and PAI-1 is more extensive than the interaction between t-PA and its true substrate plasminogen.

In order to determine whether or not mutant t-PA(Del$_{296}$-302) also exhibited resistance to the complex mixture of serine protease inhibitors present in human plasma, a 1:100 dilution of human plasma was substituted for the partially-purified recombinant PAI-1 in the protocol described above. Under these conditions, approximately 70% of the activity of the wild-type t-PA was inhibited while the activity of t-PA(Del$_{296}$-302) was unaffected.

In addition, wild-type t-PA and t-PA(Del$_{296}$-302) were incubated with undiluted human plasma and then the mixtures were acidified to pH 5.0 and centrifuged for 5 minutes at 12,000×g. The clarified supernatants were diluted and assayed for residual t-PA activity which totalled 90% for the mutant t-PA(Del$_{296}$-302) and 20% or less for the wild-type t-PA. The above results demonstrate that mutant t-PA(Del$_{296}$-302) is resistant to the complex mixture of serine protease inhibitors present in human plasma and therefore is believed to be superior to wild-type t-PA as a therapeutic agent.

G. Additional t-PA Mutants

The data presented in Section F above demonstrate that residues 296–302 and 304 of t-PA play an important role in interaction of the enzyme with the cognate inhibitor, PAI-1, but not with the substrate, Lys-plasminogen. Modeling of the catalytic domain of t-PA based on the known structure of trypsin suggests that residues 296–302 form a surface loop at the edge of the enzyme's active site. This loop is highly positively charged. As discussed above in Sections A and F, it has been proposed in the present invention that the effect of this region may be mediated by its formation of electrostatic bonds with PAI-1. To test this hypothesis, each of the charged residues within the loop were altered and the effect of these mutations upon the enzyme's interaction with PAI-1 was assessed as described below. If the positively charged residues in the loop form salt bridges with a complementary region of the serine protease inhibitor, PAI-1, then their substitution by negatively charged residues would be expected to be disruptive of interactions between t-PA and PAI-1 due to the juxtaposition of the side chains of similarly charged residues during the association of these two proteins.

More specifically, site directed mutagenesis was carried out as described above in Section B and used to construct cDNAs that encoded t-PA mutants in which Lys296, Arg$_{298}$, or Arg$_{299}$ had been replaced by a Glu residue. A cDNA encoding a triple mutant of t-PA in which all three of these residues were replaced by Glu was also constructed. Two additional cDNA's were produced; one encodes a t-PA mutant in which His$_{297}$ has been replaced by a Tyr residue while the other encodes an enzyme in which Pro$_{301}$ has been replaced by Gly.

The sequences of the six mutagenic primers employed to construct these t-PA mutants were:

t-PA($K_{296} \rightarrow E$): 5'-ATCTTTGCCGAGCACAGGA-3' t-PA($H_{297} \rightarrow Y$): 5'-TTTGCCAAGTACAGGAGGT-3' t-PA($R_{298} \rightarrow E$): 5'-GCCAAGCACGAGAGGTCGCCC-3' t-PA($R_{299} \rightarrow E$): 5'-AAGCACAGGGAGTCGCCCGG-3' t-PA($P_{301} \rightarrow G$): 5'-AGGAGGTCGGGCGGAGAGCG-3' t-PA($K_{296}$, $R_{298}$, $R_{299} \rightarrow$E, E, E): 5'-GCCATCTTTGCCGAGCAC-GAGGAGTCGCCCGGAGA-3' cDNAs encoding the mutated enzymes t-PA($K_{296} \rightarrow E$), t-PA($H_{297} \rightarrow Y$), t-PA($R_{298} \rightarrow E$) and t-PA($P_{301} \rightarrow G$) were ligated into the transient expression vector pSVT7(RI⁻), as described above.

cDNAs encoding the mutated enzymes t-PA($K_{296}$, $R_{298}$, $R_{299} \rightarrow$E, E, E) and t-PA($R_{299} \rightarrow E$) were ligated into the transient expression vector pSTE. pSTE is a derivative of pSVT7 and was constructed by replacement of the 350 bp ClaI-HindIII promoter/origin fragment of pSTV7 with the 418 bp HpaII-HindIII fragment from the promoter/origin region of SV40 cs1085 (DiMaio, D. et al, *J. Mol. Biol.*, 140:129–142 (1980)).

The resulting plasmids were designated pSVT7 (RI⁻)/t-PA($K_{296} \rightarrow E$), pSVT7(RI⁻)/t-PA($H_{297} \rightarrow Y$); pSVT7 (RI⁻)/t-PA($R_{298} \rightarrow E$); pSTE/t-PA($R_{299} \rightarrow E$); pSVT7 (RI)/t-PA($R_{301} \rightarrow G$); and pSTE/t-PA($K_{296}$, $R_{298}$, $R_{299} \rightarrow$E, E, E).

*E. coli* strain DH-1 (Hanahan, D. et al, *DNA Cloning*, Volume 1, Ed. Glover, D. M., I.R.L. Press, Oxford, pages 109–135 (1985)) was transformed with the above mutant plasmids and the resulting strains were designated pSVT7(RI⁻)/t-PA($K_{296} \rightarrow E$) [DH-1], pSVT7(RI⁻)/t-PA($H_{297} \rightarrow Y$) [DH-1]; pSVT7(RI⁻)/t-PA($R_{298} \rightarrow E$) [DH-1]; pSTE/t-PA($R_{299} \rightarrow E$) [DH-1]; pSVT7(RI⁻)/t-PA($R_{301} \rightarrow G$) [DH-1]; and pSTE/t-PA($K_{296}$, $R_{298}$, $R_{299} \rightarrow$E, E, E) [DH-1], respectively. The presence of the correct fragment was confirmed by hybridization to the appropriate radiolabeled mutagenic oligonucleotide and the orientation of the fragment was verified by restriction mapping and DNA sequencing, using the appropriate mutagenic oligonucleotides as primers.

pSVT7(RI⁻)/t-PA($R_{298} \rightarrow E$) [DH-1]; pSTE/t-PA($R_{299} \rightarrow E$) [DH-1]; and pSTE/t-PA($K_{296}$, $R_{298}$, $R_{299} \rightarrow$E, E, E) [DH-1] have been deposited on Oct. 27, 1989 at the American Type Culture Collection, 12301 Parklawn Dr., Rockville, Md. 20852 under ATCC Nos. 68157, 68154, and 68153, respectively.

The above plasmid DNAs were then used to transfect COS cells as described above. Assays were performed as described above with both dilutions of the resulting conditioned media (typically 1:300) and with immuno-purified enzymes.

Next, the $K_m$ and $K_{cat}$ values of the wild-type and mutant t-PAs were determined by assaying the various forms of the enzyme in the presence of saturating concentrations of Des-A-fibrinogen (25 µg/ml) and different concentrations (from 0.02–0.16 µM) of the substrate, Lys-plasminogen. The results are shown in Table XI below.

TABLE XI

| Enzyme | $K_m$ (µM) | $K_{cat}$ (s⁻¹) |
|---|---|---|
| Wild-type t-PA | 0.024 | 0.22 |
| t-PA($K_{296} \rightarrow E$) | 0.026 | 0.22 |
| t-PA($H_{297} \rightarrow Y$) | 0.017 | 0.14 |
| t-PA($R_{298} \rightarrow E$) | 0.027 | 0.24 |
| t-PA($R_{299} \rightarrow E$) | 0.033 | 0.26 |
| t-PA($P_{301} \rightarrow G$) | 0.027 | 0.24 |
| t-PA($K_{296}$, $R_{298}$, $R_{299} \rightarrow$ E, E, E) | 0.027 | 0.24 |

As shown in Table XI above, none of the mutations discussed above substantially altered the t-PA's interaction with its substrate.

Figure 6:
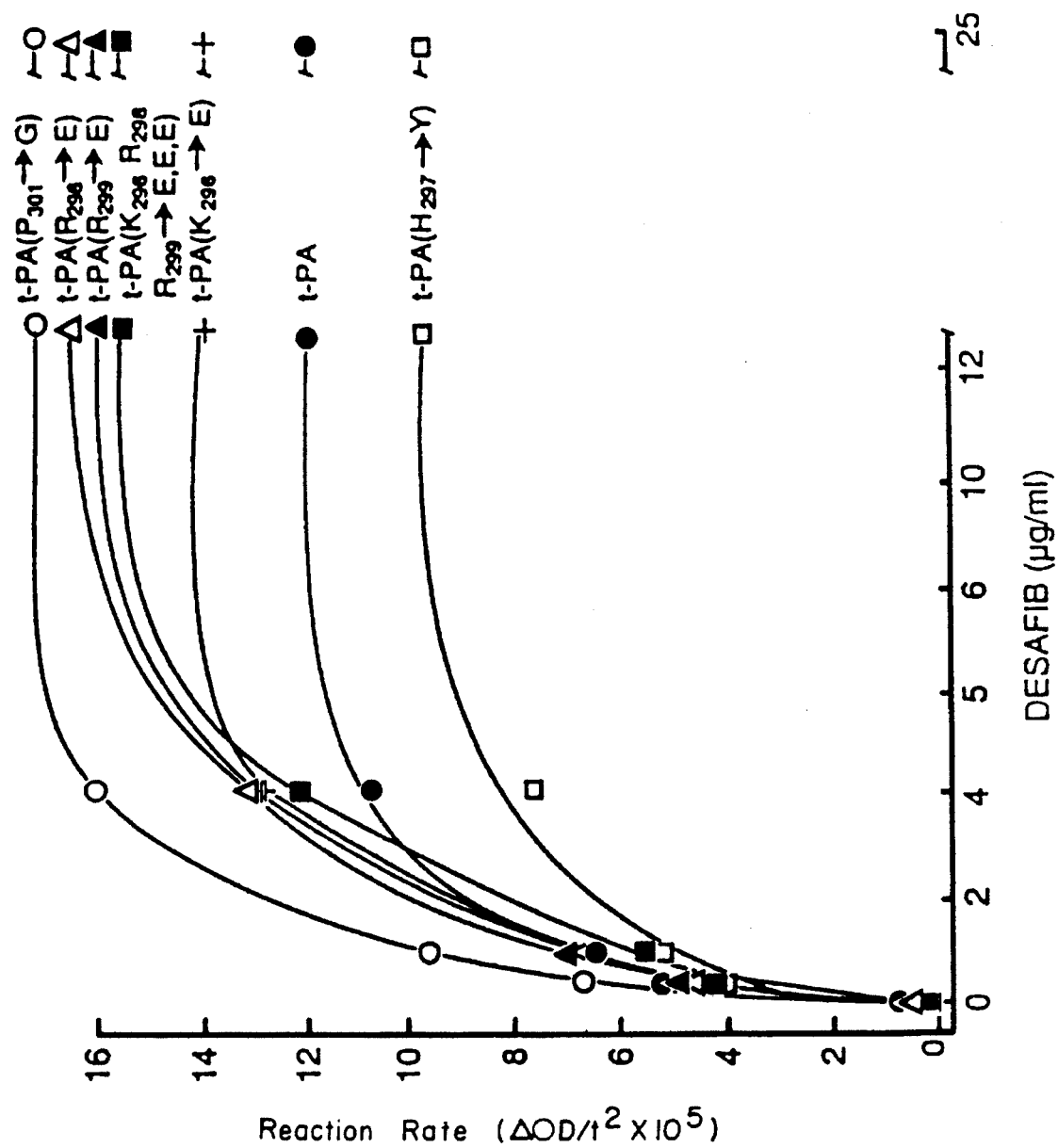
Figure 7:
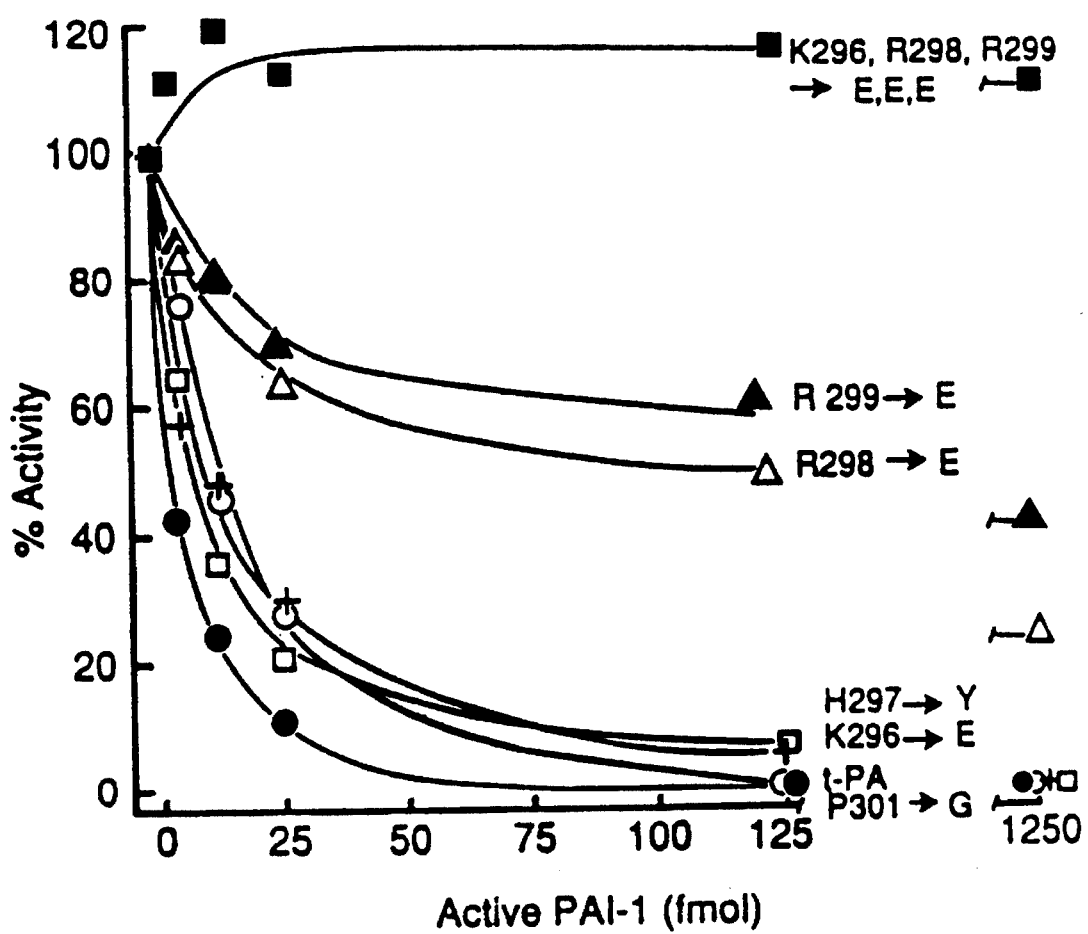

Similarly, the data presented in FIG. 6 suggests that the mutations have not altered t-PA's interaction with its positive effector, Des-A-fibrinogen. By contrast, the data presented in FIG. 7 indicates clear differences in the behavior of wild-type t-PA and some of the mutant t-PAs. Specifically, the ability to interact normally with the serpin, PAI-1, has been substantially changed for three of the mutant t-PAs, i.e., t-PA($R_{298} \rightarrow E$), t-PA($R_{299} \rightarrow E$), and t-PA($K_{296}$, $R_{298}$, $R_{299} \rightarrow$E, E, E). The behavior of the triple mutant is particularly striking; even after pre-incubation with a greater than 200-fold molar excess of PAI-1, the triple mutant shows no loss of activity. These findings support the proposal that the surface loop of t-PA, i.e., residues 296–302, interacts specifically with the cognate inhibitor, PAI-1, and suggest that this interaction involves $Arg_{298}$ and $Arg_{299}$. These observations are consistent with the hypothesis that the specific interactions between t-PA and PAI-1 involve electrostatic bonds. The residues of t-PA involved in these interactions are $Arg_{298}$, $Arg_{299}$, and $Arg_{304}$.

EXAMPLE 2

PAI-1 MUTANTS

Although the technology described in this example is directed to the use of t-PA as the serine protease and PAI-1 as the serine protease inhibitor, other serine proteases of the chymotrypsin superfamily, such as those described above, and other serine protease inhibitors, such as those described above, could easily and readily be employed using the techniques described herein without departing from the spirit and scope of this invention.

A. Expression, Purification and Assay of Glycosylated PAI-1 in Eukaryotic Cells

Two different cDNA clones derived from the 3.2 kb and 2.2 kb mRNAs encoding PAI-1 (Ny, T. et al, *Proc. Natl. Acad. Sci. USA*, 83:6776–6780 (1986); and Pannekoek, H. et al, *EMBO J.*, 5:2539–2544 (1986)) were used to construct a full length cDNA in a mammalian expression vector. The first clone, lambda PAI-1, was a truncated version of the cDNA that was obtained by screening a human placental cDNA library (provided by Dr. Carol Mendelson, Department of Biochemistry, Southwestern Medical Center, Dallas, Tex.) with a synthetic oligonucleotide corresponding to the following sequence of 8 amino acids of PAI-1 (AVDQLTRL) (Ny, T. et al, *Proc. Natl. Acad. Sci. USA*, 83:6776–6780 (1986); and Pannekoek, H. et al, *EMBO J.*, 5:2539–2544 (1986)). The fragment of DNA released from this clone by digestion with EcoRI corresponded to nucleotides 147–2013 of the PAI-1 sequence reported by Ny, T. et al, *Proc. Natl. Acad. Sci. USA*, 83:6776–6780 (1986). This fragment was subcloned into the plasmid vector pUC 18

(Yanisch-Perron, C. et al, *Gene*, 33:103–119 (1985)) to yield the recombinant plasmid pPAI-1. The insert from this plasmid was then used to screen a human endothelial cell cDNA library that was constructed in bacteriophage lambda gt11 (Huynh, T. et al, *DNA Cloning*, Volume 1, Ed. Glover, D. M., I.R.L. Press, Oxford, pages 49–88 (1985)). One of the cDNA clones isolated in this fashion, i.e., lambda PAI-1-11A, carries an insert that is identical in sequence to the PAI-1 cDNA previously reported (Pannekoek, H. et al, *EMBO J.*, 5:2539–2544 (1986)) except for the presence of two additional nucleotides at the 5' end. The EcoRI-BglII fragment derived from the 5' end of this clone, nucleotides 52–1479, was fused to the 3' BglII-EcoRI fragment of pPAI-1 to yield pPAI-1-RBR.

The SV40 vector used to express PAI-1 in mammalian cells was constructed as follows. The termini of the EcoRI fragment released from pPAI-1-RBR were filled with the Klenow fragment of *E. coli* DNA polymerase, ligated to synthetic XbaI linkers and inserted in place of the t-PA fragment in the plasmid pSV/t-PA3 to yield $pSV_L$-PAI-1 (Sambrook, J. et al, *Mol. Biol. Med.*, 3:459–481 (1986)). Stocks of $SV_L$-PAI-1 were generated and propagated as described by Doyle, C. et al, *J. Cell. Biol.*, 105:704–714 (1985).

PAI-1 clones described previously by Pannekoek, H. et al, *EMBO J.*, 5:2539–2544 (1986) and Ginsberg, D. et al, *J. Clin. Invest.* 78:1673–1680 (1986) encode a PAI-1 protein identical in sequence to that encoded by pPAI-1-RBR and could have been used in place of pPAI-1-RBR to construct $SV_L$-PAI-1.

Monolayers of CV-1 simian cells were grown at 37° C. and then infected with $SV_L$-PAI-1. After 24 hours, the medium was replaced with serum-free Dulbecco's medium (GIBCO, Inc.) and incubation was continued for a further 48 hours. The supernatant medium containing secreted PAI-1 was then filtered through an 0.45 micron filter (Nalge Co.). Nonidet P40 (Sigma Chemical Co.) and 1.0M sodium phosphate (pH 7.2) buffer were then added to concentrations of 0.1% (v/v) and 10 mM, respectively. The stabilized medium was applied to an affinity column of concanavalin A-Sepharose 4B (1.0 ml packed bed volume), which had been equilibrated with a buffer comprising 20 mM sodium phosphate (pH 7.2), 135 mM NaCl, 7.0 mM KCl (hereinafter "PBS"), at a flow rate of 50 ml per hour. The column was successively washed with 25 volumes of PBS containing 0.1% (v/v) of Nonidet P40, 25 volumes of PBS containing 0.1% (v/v) of Nonidet P40 and 1.0M NaCl and finally with 10 volumes of 20 mM sodium phosphate buffer (pH 7.2). The bound PAI-1 was specifically eluted with 0.5M alpha-methyl-D-glucoside (Sigma Chemical Co.) in 20 mM sodium phosphate buffer (pH 7.2). Fractions containing PAI-1 (as assayed by inhibition of urokinase from Calbiochem, Inc. in the indirect chromogenic assay described above) were pooled. Nonidet P40 was then added to a concentration of 0.1% (v/v) and 0.57 g of guanidine hydrochloride (U.S. Biochemicals) was added per ml of pooled eluate. The partially-purified PAI-1 thus obtained was dialyzed against a buffer comprising 20 mM sodium phosphate (pH 7.2) and 10% (v/v) glycerol, and was stored in aliquots at −80° C. until used.

The PAI-1 prepared in this manner contained 40 μg/ml of total protein (assayed by Bradford's reagent purchased from BioRad Inc.) and 15 μg/ml of PAI-1, as assayed by staining of 12.5% (w/v) SDS-polyacrylamide gels. Titration against urokinase (itself titrated to be 52% active using $^3$H-diisopropylfluorophosphate (NET-065 from New England Nuclear, Inc.)) revealed that the PAI-1 prepared as described herein was 16.6% active and that the concentration of active PAI-1 was 48 nM.

B. Selection of PAI-1 Sites for Mutagenesis

To test the hypothesis that residues $Glu_{350}$ and $Glu_{351}$ of PAI-1 interact with t-PA, oligonucleotide directed mutagenesis was used to produce the two mutant forms of PAI-1 shown in Table XII below.

TABLE XII

| | 346. . 355 |
|---|---|
| wild-type PAI-1 | RMAPEEIIMD |
| PAI-1($E_{350}$->R) | RMAP R EIIMD |
| PAI-1($E_{351}$->R) | RMAPE R IIMD |

Mutants PAI-1($E_{350}$→R) and PAI-1($E_{351}$→R) contain substitutions of Arg for $Glu_{350}$ and $Glu_{351}$, respectively, and were chosen to selectively alter the negatively-charged Glu residues to positively-charged Arg residues and promote potential interactions with the negatively-charged $Glu_{304}$ residue present in t-PA($R_{304}$→E). A variety of other substitutions could be made for $Glu_{350}$ which would produce a PAI-1 with increased interaction with, e.g., the t-PA($R_{304}$→E) mutant, provided those substitutions were complementary to the specific mutations introduced in residue $Arg_{304}$ of t-PA without departing from the spirit and scope of the present invention.

C. Oligonucleotide-Mediated Mutagenesis of PAI-1

First, it was necessary to construct a PAI-1 expression plasmid, designated plasmid pPAIST7, which provides for the direct expression of methionyl-PAI-1 while eliminating the signal sequence and the 3'-untranslated region of the cDNA sequence from the expression vector. To achieve this, synthetic DNA linkers were used to reconstruct both ends of the PAI-1 cDNA coding sequence and to introduce an ATG protein synthesis initiation codon immediately before the triplet encoding the first residue of mature PAI-1. In addition, to facilitate the insertion of the cDNA coding region into plasmid pBR322, the linkers were designed to generate EcoRI and HindIII restriction endonuclease recognition sites at the 5' and 3' termini, respectively, of the PAI-1 cDNA fragment.

More specifically, plasmid pPAIST7 was obtained by digesting pPAI-1-RBR with ApaLI and PflMI. The resulting 1127 bp fragment, containing 2 bp of the codon for residue 1 of PAI-1 and the full coding sequence for residues 2–376 of the 379 residue protein, was purified by gel electrophoresis. Next, synthetic linkers (10 bp at the 5' end and 13 bp at the 3' end) were ligated with the 1127 bp ApaLI and PflMI DNA fragment, digested with EcoRI and HindIII, and the 1146 bp EcoRI- and HindIII-digested DNA fragment was isolated by gel electrophoresis. This fragment was then cloned into EcoRI- and HindIII-digested pBR322.

To initiate construction of an expression plasmid, the subclone was digested with EcoRI and the linear plasmid dephosphorylated with bacterial alkaline phosphatase. Then, using the 360 bp EcoRI DNA fragment from pC5A-48 (Franke, A. et al, *Meth. Enzymol.*, 162:653–668 (1988)), containing the trp promoter and ribosome binding site, a PAI-1 expression plasmid was constructed by ligating the two fragments together. Next, *E. coli* were transformed with the resulting plasmids as described by Maniatis, T. et al, *Molecular Cloning: A Laboratory Manual*, 1st Edition, Cold Spring Harbor (1982). The plasmid DNA of the resulting transformants was screened by restriction analysis with HindIII for the presence and orientation of the trp promoter fragment. Multiple transformants were identified containing plasmids having the PAI-1 gene adjacent to the trp promoter in the configuration required for direct expression of the inhibitor. One such plasmid was designated pPAIST7.

Figure 8:
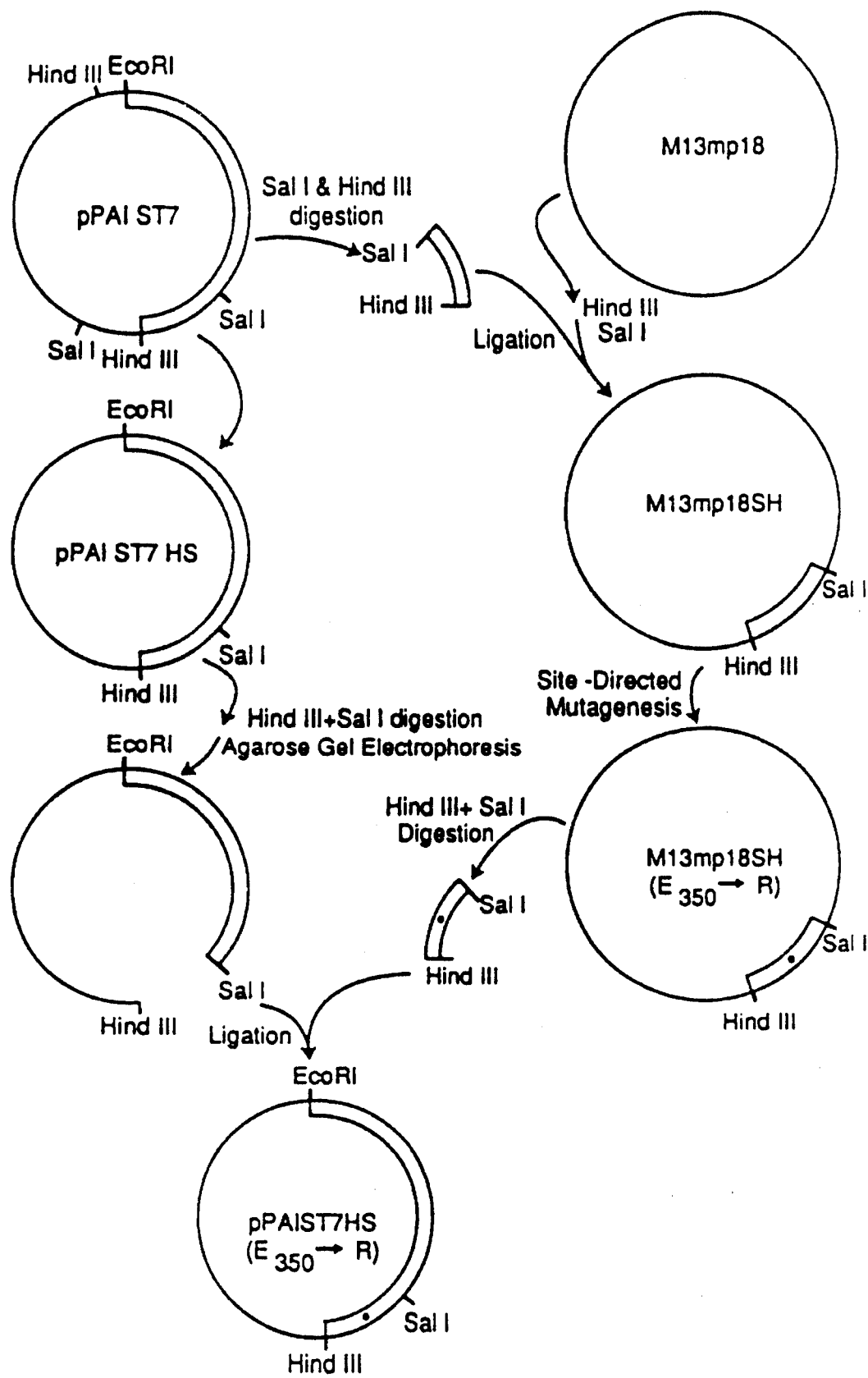

The SalI-HindIII fragment of plasmid pPAIST7, containing the nucleotide sequences of PAI-1 encoding amino acid residues $Val_{284}$ to $Pro_{379}$, was ligated into SalI-HindIII digested replicative form M13mp18 (see FIG. 8). The ligated DNA was transfected into *E. coli* strain TG-1. White plaques formed by recombinant bacteriophage were picked and the presence of the appropriate 290 base pair SalI-HindIII fragment was verified by Southern hybridization, restriction mapping and DNA sequencing.

Mutations in the 290 base pair SalI-HindIII fragment were introduced using 5'-phosphorylated synthetic mutagenic oligonucleotide primers as described for t-PA above (see FIG. 8). The sequences of the two mutagenic primers employed to construct these PAI-1 mutants were:

PAI-1($E_{350}\rightarrow R$): 5' TGATGATCTCTCTTGGGGC 3'

PAI-1($E_{351}\rightarrow R$): 5' CCATGATGATTCTCTCGGGG 3'

The sequences of the resulting mutant SalI-HindIII fragments of PAI-1 DNA were completely determined. The doubled-stranded replicative form of the DNAs of proven mutants was then isolated and the mutated 290 base pair SalI-HindIII fragments were isolated by SalI-HindIII digestion and electrophoresis through 6.0% (w/v) non-denaturing polyacrylamide gels. As described in detail below, these fragments, containing mutations, were then used to reconstruct versions of the PAI-1 cDNA that encoded the PAI-1 mutants of interest.

D. Construction of Expression Vectors for Mutant PAI-1's

Mutants of PAI-1 in plasmid pPAIST7HS (a derivative of plasmid pPAIST7 lacking the HindIII site at nucleotide pair 1 and the SalI site at nucleotide pair 2106, which was constructed to facilitate the exchange of mutated SalI to HindIII fragments in the PAI-1 cDNA coding sequences, (see FIG. 8) were constructed as follows:

The central 290 base pair SalI to HindIII fragment of the PAI-1 cDNA was removed from plasmid pPAIST7HS by digestion with SalI and HindIII and by 1.0% (w/v) agarose gel electrophoresis. The remaining linear-fragment of the vector DNA was then ligated to the mutant versions of the 290 base pair SalI to HindIII fragment described above which had been generated by oligonucleotide-directed mutagenesis (see FIG. 8). The resulting plasmids were designated pPAIST7HS($E_{350}\rightarrow R$) and pPAIST7HS($E_{351}\rightarrow R$).

*E. coli* strain DH-1 (Hanahan, D. et al, *DNA Cloning*, Volume 1, Ed. Glover, D. M., I.R.L. Press, Oxford, pages 109–135 (1985)) was transformed with the above mutant plasmids and the resulting strains were designated pPAIST7HS [DH-1]; pPAIST7HS($E_{350}\rightarrow R$) [DH-1]; and pPAIST7HS($E_{351}\rightarrow R$) [DH-1], respectively. *E. coli* strain TG-1 (Gibson, T., Thesis, University of Cambridge, England (1984)) was transformed with the above mutant plasmids and the resulting strains were designated pPAIST7HS [TG-1]; pPAIST7HS($E_{350}\rightarrow R$) [TG-1]; and pPAIST7HS($E_{351}\rightarrow R$) [TG-1], respectively. The presence of the correct fragment was confirmed by hybridization to the appropriate radiolabeled mutagenic oligonucleotide and by nucleic acid sequencing.

pPAIST7HS($E_{350}\rightarrow R$) [DH-1]; and pPAIST7HS($E_{351}\rightarrow R$) [DH-1] have been deposited at the American Type Culture Collection under ATCC Nos. 68155 and 68156, respectively.

E. Expression, Extraction, and Assay of Wild-Type and Mutant PAI-1s

*E. coli* strains pPAIST7HS [TG-1], pPAIST7HS($E_{350}\rightarrow R$) [TG-1], and pPAIST7HS($E_{351}\rightarrow R$) [TG-1] were grown overnight at 37° C. in Luria-Bertani broth to saturating density. 50 μl of culture were used to inoculate 50 ml of modified M9 medium (pH 7.4) containing, per liter, 6.0 g of $Na_2HPO_4$, 3.0 g of $KH_2PO_4$, 0.5 g of NaCl, 0.5 g of $MgSO_4.7H_2O$, 1.0 g of $NH_4Cl$, 5.0 g of casamino acids, 10.0 g of glucose, 10.0 ml of glycerol, 1.0 mg of thiamine-HCl, and 25 mg of ampicillin. Bacterial cultures were grown for 22 hours at 37° C. in 250 ml Ehrlenmeyer flasks. Cell extracts were prepared from cultures as follows.

*E. coli* were pelleted by centrifugation, washed in 20 ml of cold 50 mM Tris-HCl (pH 8.0) and 1.0 mM EDTA by centrifugation, and resuspended in 3.6 ml of the same buffer on ice, Extraction was accomplished by the addition of 0.4 ml of 10 mg per ml of lysozyme for 20 minutes 0.1 ml of 10% (v/v) Nonidet P-40 for 10 minutes, and 0.2 ml of 5.0M NaCl for 10 minutes. The cells were briefly disrupted using the microtip of a sonifier/cell disruptor at 50% duty cycle and setting 7 (Branson Sonic Power Company) to reduce the viscosity before centrifugation at 15,000×g for 30 minutes at 4° C. Glycerol was added to the clarified bacterial lysates to a concentration of 10% (v/v) and the extracts containing PAI-1 were stored at −80° C. in aliquots until used.

Extracts were titrated for active PAI-1 by incubation for 3 hours at 24° C. with urokinase as described above for PAI-1 expressed in mammalian cells. Extracts of wild-type PAI-1, PAI-1($E_{350}\rightarrow R$), and PAI-1($E_{351}\rightarrow R$) contained 803 nM, 593 nM, and 162 nM of active PAI-1, respectively.

Kinetic measurements on the rate of interaction of wild-type and mutant t-PAs with wild-type and mutant PAI-1s were performed at 24° C. in 0.1M Tris-HCl buffer (pH 7.4) containing 0.1 mM EDTA and 0.1% (v/v) Tween 20. The indirect chromogenic assay for t-PA described above was used to determine the residual enzyme activity remaining as a function of time. Under pseudo-first order conditions for an excess of PAI-1 over t-PA, the half-life ($t_{1/2}$) was determined for each inhibitor concentration from the slope of a linear semi-logarithmic plot of residual t-PA activity versus time. The rate constant, $k_1$, was then calculated by dividing the apparent rate constant ($k_{app}=0.693/t_{1/2}$) by the inhibitor concentration.

The rate of inhibition of 60 pM t-PA was studied under pseudo-first order conditions using inhibitor concentrations ranging from 0.6 to 100 nM. The t-PA-PAI-1 mixes were preincubated in microtiter plate wells at 24° C. for various time periods (from 0 to 30 minutes) before the addition of a mixture of Lys-plasminogen, Spectrozyme PL, and Des-A-fibrinogen to final concentrations of 300 nM, 0.4 nM, and 12.5 μg/ml, respectively. After the addition of substrates, the microtiter plates were incubated at 37° C. and the absorbance at 405 nm was monitored for 2 hours to determine the residual t-PA activity.

The approximate rate constants of inhibition ($M^{-1}s^{-1}$) of wild-type and mutant t-PAs by wild-type and mutant PAI-1s are given in Table XIII below.

TABLE XIII

|  | wild-type t-PA | t-PA($R_{304}\rightarrow S$) | t-PA($R_{304}\rightarrow E$) |
| --- | --- | --- | --- |
| wild-type PAI-1 | $1 \times 10^6$ | $3 \times 10^5$ | $1 \times 10^4$ |
| PAI-1($E_{350}\rightarrow R$) | $1 \times 10^6$ | $1 \times 10^6$ | $1 \times 10^6$ |
| PAI-1($E_{351}\rightarrow R$) | $3 \times 10^5$ | $1 \times 10^5$ | $1 \times 10^5$ |

As shown in Table XIII above, both PAI-1($E_{350} \rightarrow R$) and PAI-1($E_{351} \rightarrow R$) show increased rate constants of interaction with t-PA($R_{304} \rightarrow E$) in comparison to wild-type PAI-1, proving that the mutations have restored the ability of PAI-1 to inhibit the serine protease inhibitor-resistant t-PA($R_{304} \rightarrow E$).

While this invention has been described in detail and with reference to specific embodiments thereof, it will be apparent to one skilled in the art that various changes and modifications could be made therein without departing from the spirit and scope thereof.

We claim:

1. A t-PA mutant which is resistant to inhibition by its cognate inhibitor, wherein said t-PA mutant has an acidic or neutral amino acid substitution at the basic amino acid corresponding to position 304 of human t-PA.

2. The t-PA mutant as claimed in claim 1, wherein said t-PA mutant is t-PA($R_{304} \rightarrow S$) or t-PA($R_{304} \rightarrow E$).

3. The t-PA mutant as claimed in claim 1, wherein said cognate inhibitor is selected from the group consisting of PAI-1, PAI-2 and PAI-3.

4. The t-PA mutant as claimed in claim 3, wherein said cognate inhibitor is PAI-1.

5. A t-PA mutant which is resistant to inhibition by its cognate inhibitor, wherein said t-PA mutant has an acidic or neutral amino acid substitution at at least one of the basic amino acid corresponding to position 298 of human t-PA and the basic amino acid corresponding to position 299 of human t-PA.

6. The t-PA mutant as claimed in claim 5, wherein said t-PA mutant is t-PA($R_{298} \rightarrow E$) or t-PA($R_{299} \rightarrow E$).

7. The t-PA mutant as claimed in claim 5, wherein said t-PA mutant also has an acidic or neutral amino acid substitution at the basic amino acid corresponding to position 296 of human t-PA.

8. The t-PA mutant as claimed in claim 7, wherein said t-PA mutant is t-PA($K_{296}$, $R_{298}$, $R_{299} \rightarrow E$, E, E).

9. The t-PA mutant as claimed in claim 5, wherein said cognate inhibitor is selected from the group consisting of PAI-1, PAI-2 and PAI-3.

10. The t-PA mutant as claimed in claim 9, wherein said cognate inhibitor is PAI-1.

11. The t-PA mutant as claimed in claim 5, wherein said t-PA mutant has an acidic or neutral amino acid substitution at each of the amino acids corresponding to positions 296, 297, 298 and 299 of human t-PA.

12. A t-PA mutant which is resistant to inhibition by its cognate inhibitor, wherein said t-PA mutant is t-PA($Del_{296-302}$).

13. A gene encoding a t-PA mutant which is resistant to inhibition by its cognate inhibitor, wherein said t-PA mutant has an acidic or neutral amino acid substitution at the basic amino acid corresponding to position 304 of human t-PA.

14. The gene as claimed in claim 13, wherein said t-PA mutant is t-PA($R_{304} \rightarrow S$) or t-PA($R_{304} \rightarrow E$).

15. The gene as claimed in claim 13, wherein said cognate inhibitor is selected from the group consisting of PAI-1, PAI-2 and PAI-3.

16. The gene as claimed in claim 15, wherein said cognate inhibitor is PAI-1.

17. A gene encoding a t-PA mutant which is resistant to inhibition by its cognate inhibitor, wherein said t-PA mutant has an acidic or neutral amino acid substitution at at least one of the basic amino acid corresponding to position 298 of human t-PA and the basic amino acid corresponding to position 299 of human t-PA.

18. The gene as claimed in claim 17, wherein said t-PA mutant is t-PA($R_{298} \rightarrow E$) or t-PA($R_{299} \rightarrow E$).

19. The gene as claimed in claim 17, wherein said t-PA mutant also has an acidic or neutral amino acid substitution at the basic amino acid corresponding to position 296 of human t-PA.

20. The gene as claimed in claim 19, wherein said t-PA mutant is t-PA($K_{296}$, $R_{298}$, $R_{299} \rightarrow E$, E, E).

21. The gene as claimed in claim 17, wherein said cognate inhibitor is selected from the group consisting of PAI-1, PAI-2 and PAI-3.

22. The gene as claimed in claim 21, wherein said cognate inhibitor is PAI-1.

23. The gene as claimed in claim 17, wherein said t-PA mutant has an acidic or neutral amino acid substitution at each of the amino acids corresponding to positions 296, 297, 298 and 299 of human t-PA.

24. A gene encoding a t-PA mutant which is resistant to inhibition by its cognate inhibitor, wherein said t-PA mutant is t-PA($Del_{296-302}$).

25. A method for obtaining a t-PA mutant which is resistant to inhibition by its cognate inhibitor comprising:

(A) culturing a host cell which has been transformed with DNA comprising a, gene encoding said t-PA mutant, wherein said t-PA mutant has an acidic or neutral amino acid substitution at the basic amino acid corresponding to position 304 of human t-PA; and (B) isolating the resulting t-PA mutant.

26. The method as claimed in claim 25, wherein said t-PA mutant is t-PA($R_{304} \rightarrow S$) or t-PA($R_{304} \rightarrow E$).

27. The method as claimed in claim 25, wherein said cognate inhibitor is selected from the group consisting of PAI-1, PAI-2 and PAI-3.

28. The method as claimed in claim 27, wherein said cognate inhibitor is PAI-1.

29. A method for obtaining a t-PA mutant which is resistant to inhibition by its cognate inhibitor comprising:

(A) culturing a host cell which has been transformed with DNA comprising a gene encoding said t-PA mutant, wherein said human t-PA mutant has an acidic or neutral amino acid substitution at at least one of the basic amino acid corresponding to position 298 of human t-PA and the basic amino acid corresponding to position 299 of human t-PA; and (B) isolating the resulting t-PA mutant.

30. The method as claimed in claim 2, wherein said t-PA mutant is t-PA($R_{298} \rightarrow E$) or t-PA($R_{299} \rightarrow E$).

31. The method as claimed in claim 29, wherein said t-PA mutant also has an acidic or neutral amino acid substitution at the basic amino acid corresponding to position 296 of human t-PA.

32. The method as claimed in claim 31, wherein said t-PA mutant is t-PA($K_{296}$, $R_{298}$, $R_{299} \rightarrow E$, E, E).

33. The method as claimed in claim 29, wherein said cognate inhibitor is selected from the group consisting of PAI-1, PAI-2 and PAI-3.

34. The method as claimed in claim 33, wherein said cognate inhibitor is PAI-1.

35. The method as claimed in claim 29, wherein said t-PA mutant has an acidic or neutral amino acid substitution at each of the amino acids corresponding to positions 296, 297, 298 and 299 of human t-PA.

36. A method for obtaining a t-PA mutant which is resistant to inhibition by its cognate inhibitor comprising:

(A) culturing a host cell which has been transformed with DNA comprising a gene encoding said t-PA mutant, wherein said t-PA mutant is t-PA ($Del_{296-302}$); and (B) isolating the resulting t-PA mutant.

37. Plasmid pSVT7(RI⁻)/t-PA(R$_{304}$→S).
38. Plasmid pSVT7(RI⁻)/t-PA(R$_{304}$→E).
39. Plasmid pSVT7(RI⁻)/t-PA(Del$_{296-302}$).
40. Plasmid pSVT7(RI⁻)/t-PA(R$_{298}$→E).
41. Plasmid pSTE/t-PA(R$_{299}$→E).
42. Plasmid pSTE/t-PA(K$_{296}$, R$_{298}$, R$_{299}$→E, E, E).
43. pSVT7(RI⁻)/t-PA(R$_{304}$→S) [DH-1] having the identifying characteristics of ATCC No. 67894.
44. pSVT7(RI⁻)/t-PA(R$_{304}$→E) [DH-1] having the identifying characteristics of ATCC No. 67896.
45. pSVT7(RI⁻)/t-PA(Del$_{296-302}$) [DH-1] having the identifying characteristics of ATCC No. 67895.
46. pSVT7(RI⁻)/t-PA(R$_{298}$→E) [DH-1] having the identifying characteristics of ATCC No. 68157.
47. pSTE/t-PA(R$_{299}$→E) [DH-1] having the identifying characteristics of ATCC No. 68154.
48. pSTE/t-PA(K$_{296}$, R$_{298}$, R$_{299}$→E, E, E) [DH-1] having the identifying characteristics of ATCC No. 68153.

* * * * *